US009850541B2

(12) United States Patent
Ganepola

(10) Patent No.: US 9,850,541 B2
(45) Date of Patent: Dec. 26, 2017

(54) METHODS AND KITS FOR DETECTING SUBJECTS AT RISK OF HAVING CANCER

(71) Applicant: Valley Health System, Paramus, NJ (US)

(72) Inventor: Ganepola A. P. Ganepola, Hillsdale, NJ (US)

(73) Assignee: Valley Health System, Paramus, NJ (US)

( * ) Notice: Subject to any disclaimer, the term of this patent is extended or adjusted under 35 U.S.C. 154(b) by 37 days.

(21) Appl. No.: 14/364,472

(22) PCT Filed: Dec. 6, 2012

(86) PCT No.: PCT/US2012/068148
§ 371 (c)(1),
(2) Date: Jun. 11, 2014

(87) PCT Pub. No.: WO2013/095941
PCT Pub. Date: Jun. 27, 2013

(65) Prior Publication Data
US 2015/0011410 A1     Jan. 8, 2015

Related U.S. Application Data

(60) Provisional application No. 61/577,441, filed on Dec. 19, 2011.

(51) Int. Cl.
*C12Q 1/68* (2006.01)
(52) U.S. Cl.
CPC ..... *C12Q 1/6886* (2013.01); *C12Q 2600/158* (2013.01); *C12Q 2600/16* (2013.01); *C12Q 2600/178* (2013.01)

(58) Field of Classification Search
CPC combination set(s) only.
See application file for complete search history.

(56) References Cited

U.S. PATENT DOCUMENTS

| | | | |
|---|---|---|---|
| 2006/0094025 A1* | 5/2006 | Getts | C12P 19/34 435/6.14 |
| 2011/0053158 A1 | 3/2011 | Mambo et al. | |
| 2011/0171646 A1 | 7/2011 | Schmittgen et al. | |
| 2011/0275533 A1 | 11/2011 | Luthra et al. | |
| 2011/0281268 A1 | 11/2011 | Qu et al. | |
| 2013/0065778 A1* | 3/2013 | Weidhaas | C12N 15/111 506/9 |

FOREIGN PATENT DOCUMENTS

WO     2011075873 A1     6/2011

OTHER PUBLICATIONS

Morimura et al., "Novel diagnostic value of circulating miR-18a in plasma of patients with pancreatic cancer," Br. J. Cancer(Nov. 22, 2011):105(11):1733-1740.
Gui et al., "Serum microRNA characterization identifies miR-885-5p as a potential marker for detecting liver pathologies," Clin. Sci (Lond.): (Mar. 2011): 120(5):183-193.
(Continued)

*Primary Examiner* — Reza Ghafoorian
(74) *Attorney, Agent, or Firm* — Fox Rothschild LLP

(57) ABSTRACT

The present invention relates to agents and methods for screening, diagnosis and surveillance of cancer, in particular pancreatic cancer.

10 Claims, 1 Drawing Sheet

(56) References Cited

OTHER PUBLICATIONS

Kosaka et al., "Circulating microRNA in body fluid; a new potential biomarker for cancer diagnosis and prognosis," Cancer Sci., (Oct. 2010): 101(10):2087-2092.

Wang et al., "MicroRNAs in Plasma of Pancreatic Ductal Adenocarcinoma Patients as Novel Blood-Based Biomarkers of Disease," Cancer Prev Res (2009): 2(9):807-13.

Lee et al., "Expression profiling identifies microRNA singature in pancreatic cancer," Int J Cancer (2007); 120(5):1046-54.

Ho et al., "Circulating miR-210 as a Novel Hypoxia Marker in Pancreatic Cancer1," Transl Oncol. (2010); 3(2):109-13.

Ganepola et al, "Gene expression profiling of primary and metastatic colon cancers identifies a reduced proliferative rate in metastatic tumors," Clin Exp Metastasis. (2010); 27(1):1-9.

Laconti et al., "Tissue and Serum microRNAs in the KrasG12D Transgenic Animal Model and in Patients with Pancreatic Cancer," PLOS ONE (Jun. 2011); 6(6);e20687.

"GeneChip miRNA Array": URL:http://media.affymetrix.com/support/technical/datasheets/miRNA_datasheet.pdf (retrieved on Aug. 21, 2012).

Ali et al., "Differentially expressed mirnas int he plasma may provide a molecular signature for aggressive pancreatic cancer," American Jounral of Translational Research (Sep. 28, 20101); 3(1): 28-47.

Ganepola et al., Prateome analysis of pancreatic cancer tissue for identification of novel biomarkers, American Association for Cancer Research—Program and Proceedings (Oct. 8-11, 2009):C32 (2 pages).

\* cited by examiner

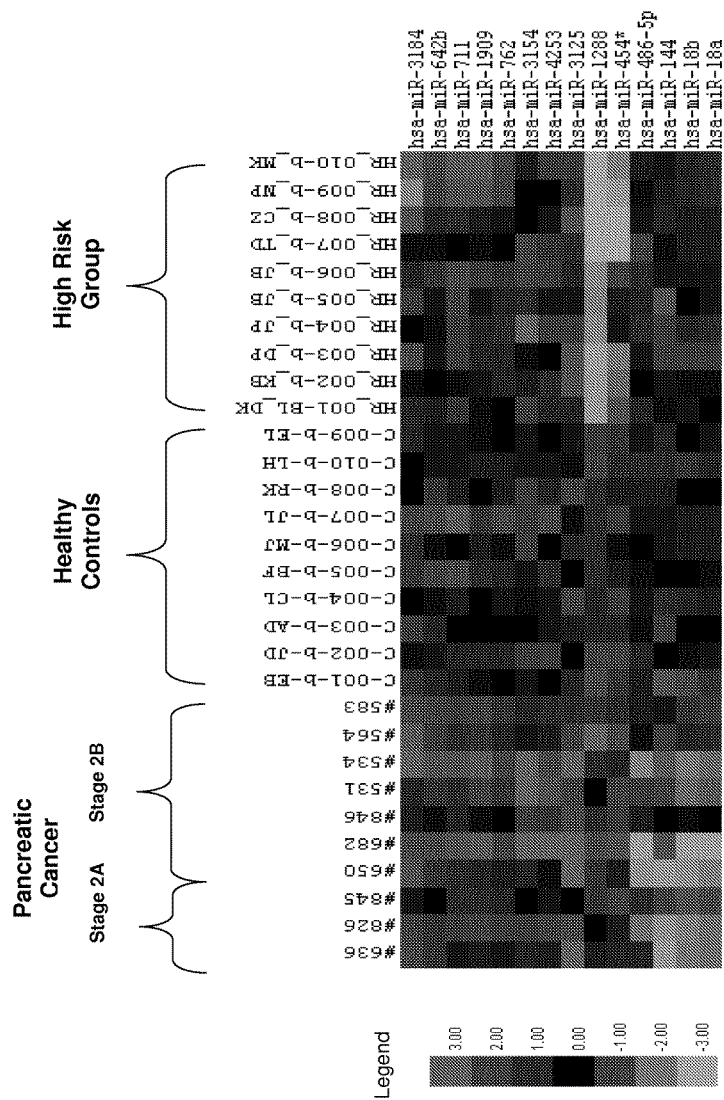

SEQUENCE LISTING

<160> NUMBER OF SEQ ID NOS: 118

<210> SEQ ID NO 1
<211> LENGTH: 23
<212> TYPE: RNA
<213> ORGANISM: Homo sapiens

<400> SEQUENCE: 1
uaaggugcau cuagugcaga uag                                          23

<210> SEQ ID NO 2
<211> LENGTH: 22
<212> TYPE: RNA
<213> ORGANISM: Homo sapiens

<400> SEQUENCE: 2
aagcugccag uugaagaacu gu                                           22

<210> SEQ ID NO 3
<211> LENGTH: 22
<212> TYPE: RNA
<213> ORGANISM: Homo sapiens

```
<400> SEQUENCE: 3
uccuguacug agcugccccg ag                                              22

<210> SEQ ID NO 4
<211> LENGTH: 22
<212> TYPE: RNA
<213> ORGANISM: Homo sapiens

<400> SEQUENCE: 4
agacacauuu ggagagggac cc                                              22

<210> SEQ ID NO 5
<211> LENGTH: 23
<212> TYPE: RNA
<213> ORGANISM: Homo sapiens

<400> SEQUENCE: 5
uggaagacua gugauuuugu ugu                                             23

<210> SEQ ID NO 6
<211> LENGTH: 22
<212> TYPE: RNA
<213> ORGANISM: Homo sapiens

<400> SEQUENCE: 6
uccauuacac uacccugccu cu                                              22

<210> SEQ ID NO 7
<211> LENGTH: 18
<212> TYPE: RNA
<213> ORGANISM: Homo sapiens

<400> SEQUENCE: 7
cggggcggca ggggccuc                                                   18

<210> SEQ ID NO 8
<211> LENGTH: 24
<212> TYPE: RNA
<213> ORGANISM: Homo sapiens

<400> SEQUENCE: 8
ugaggggccu cagaccgagc uuuu                                            24

<210> SEQ ID NO 9
<211> LENGTH: 22
<212> TYPE: RNA
<213> ORGANISM: Homo sapiens

<400> SEQUENCE: 9
cgcaggggcc gggugcucac cg                                              22

<210> SEQ ID NO 10
<211> LENGTH: 22
<212> TYPE: RNA
<213> ORGANISM: Homo sapiens

<400> SEQUENCE: 10
gggacccagg gagagacgua ag                                              22

<210> SEQ ID NO 11
<211> LENGTH: 20
<212> TYPE: RNA
<213> ORGANISM: Homo sapiens
```

-continued

<400> SEQUENCE: 11
uagaggaagc uguggagaga                                         20

<210> SEQ ID NO 12
<211> LENGTH: 23
<212> TYPE: RNA
<213> ORGANISM: Homo sapiens

<400> SEQUENCE: 12
uaaggugcau cuagugcagu uag                                     23

<210> SEQ ID NO 13
<211> LENGTH: 22
<212> TYPE: RNA
<213> ORGANISM: Homo sapiens

<400> SEQUENCE: 13
ggggcugggg ccggggccga gc                                      22

<210> SEQ ID NO 14
<211> LENGTH: 22
<212> TYPE: RNA
<213> ORGANISM: Homo sapiens

<400> SEQUENCE: 14
cagaagggga guugggagca ga                                      22

<210> SEQ ID NO 15
<211> LENGTH: 21
<212> TYPE: RNA
<213> ORGANISM: Homo sapiens

<400> SEQUENCE: 15
cggggcagcu caguacagga u                                       21

<210> SEQ ID NO 16
<211> LENGTH: 18
<212> TYPE: RNA
<213> ORGANISM: Homo sapiens

<400> SEQUENCE: 16
agggcauguc caggggu                                            18

<210> SEQ ID NO 17
<211> LENGTH: 21
<212> TYPE: RNA
<213> ORGANISM: Homo sapiens

<400> SEQUENCE: 17
uggacugccc ugaucuggag a                                       21

<210> SEQ ID NO 18
<211> LENGTH: 21
<212> TYPE: RNA
<213> ORGANISM: Homo sapiens

<400> SEQUENCE: 18
uucaaguaau ucaggauagg u                                       21

<210> SEQ ID NO 19
<211> LENGTH: 23
<212> TYPE: RNA

```
<213> ORGANISM: Homo sapiens

<400> SEQUENCE: 19 cagugcaauaguauugucaaagc                                              23

<210> SEQ ID NO 20
<211> LENGTH: 21
<212> TYPE: RNA
<213> ORGANISM: Homo sapiens

<400> SEQUENCE: 20 uaaagugcugacagugcagau                                                21

<210> SEQ ID NO 21
<211> LENGTH: 19
<212> TYPE: RNA
<213> ORGANISM: Homo sapiens

<400> SEQUENCE: 21 aagcagcugccucugaggc                                                  19

<210> SEQ ID NO 22
<211> LENGTH: 21
<212> TYPE: RNA
<213> ORGANISM: Homo sapiens

<400> SEQUENCE: 22 uuaggccgcagaucuggguga                                                21

<210> SEQ ID NO 23
<211> LENGTH: 23
<212> TYPE: RNA
<213> ORGANISM: Homo sapiens

<400> SEQUENCE: 23 caaagugcucauagugcagguag                                              23

<210> SEQ ID NO 24
<211> LENGTH: 23
<212> TYPE: RNA
<213> ORGANISM: Homo sapiens

<400> SEQUENCE: 24 caaagugcuguucgugcagguag                                              23

<210> SEQ ID NO 25
<211> LENGTH: 22
<212> TYPE: RNA
<213> ORGANISM: Homo sapiens

<400> SEQUENCE: 25 uagcagcacguaaauauuggcg                                               22

<210> SEQ ID NO 26
<211> LENGTH: 23
<212> TYPE: RNA
<213> ORGANISM: Homo sapiens

<400> SEQUENCE: 26 agaggcuuugugcggauacgggg                                              23

<210> SEQ ID NO 27
<211> LENGTH: 23
```

```
<212> TYPE: RNA
<213> ORGANISM: Homo sapiens

<400> SEQUENCE: 27
aaaagugcuu acagugcagg uag                                              23

<210> SEQ ID NO 28
<211> LENGTH: 23
<212> TYPE: RNA
<213> ORGANISM: Homo sapiens

<400> SEQUENCE: 28
caaagugcuu acagugcagg uag                                              23

<210> SEQ ID NO 29
<211> LENGTH: 21
<212> TYPE: RNA
<213> ORGANISM: Homo sapiens

<400> SEQUENCE: 29
cuccguuugc cuguuucgcu g                                                21

<210> SEQ ID NO 30
<211> LENGTH: 23
<212> TYPE: RNA
<213> ORGANISM: Homo sapiens

<400> SEQUENCE: 30
ugugcaaauc caugcaaaac uga                                              23

<210> SEQ ID NO 31
<211> LENGTH: 22
<212> TYPE: RNA
<213> ORGANISM: Homo sapiens

<400> SEQUENCE: 31
aacuggcccu caaagucccg cu                                               22

<210> SEQ ID NO 32
<211> LENGTH: 22
<212> TYPE: RNA
<213> ORGANISM: Homo sapiens

<400> SEQUENCE: 32
uguaacagca acuccaugug ga                                               22

<210> SEQ ID NO 33
<211> LENGTH: 22
<212> TYPE: RNA
<213> ORGANISM: Homo sapiens

<400> SEQUENCE: 33
ucucccaacc cuuguaccag ug                                               22

<210> SEQ ID NO 34
<211> LENGTH: 22
<212> TYPE: RNA
<213> ORGANISM: Homo sapiens

<400> SEQUENCE: 34
ccaauauuac ugugcugcuu ua                                               22

<210> SEQ ID NO 35
```

-continued

<210> SEQ ID NO 35
<211> LENGTH: 22
<212> TYPE: RNA
<213> ORGANISM: Homo sapiens

<400> SEQUENCE: 35
ugagguagua guuuguacag uu                                          22

<210> SEQ ID NO 36
<211> LENGTH: 23
<212> TYPE: RNA
<213> ORGANISM: Homo sapiens

<400> SEQUENCE: 36
agcuucuuua cagugcugcc uug                                         23

<210> SEQ ID NO 37
<211> LENGTH: 23
<212> TYPE: RNA
<213> ORGANISM: Homo sapiens

<400> SEQUENCE: 37
acaggcggcu guagcaaugg ggg                                         23

<210> SEQ ID NO 38
<211> LENGTH: 22
<212> TYPE: RNA
<213> ORGANISM: Homo sapiens

<400> SEQUENCE: 38
ccaaaacugc aguuacuuuu gc                                          22

<210> SEQ ID NO 39
<211> LENGTH: 22
<212> TYPE: RNA
<213> ORGANISM: Homo sapiens

<400> SEQUENCE: 39
ugagguagua guuugugcug uu                                          22

<210> SEQ ID NO 40
<211> LENGTH: 22
<212> TYPE: RNA
<213> ORGANISM: Homo sapiens

<400> SEQUENCE: 40
acucaaaaug ggggcgcuuu cc                                          22

<210> SEQ ID NO 41
<211> LENGTH: 22
<212> TYPE: RNA
<213> ORGANISM: Homo sapiens

<400> SEQUENCE: 41
ucaggcucag uccccucccg au                                          22

<210> SEQ ID NO 42
<211> LENGTH: 22
<212> TYPE: RNA
<213> ORGANISM: Homo sapiens

<400> SEQUENCE: 42
uccagcauca gugauuuugu ug                                          22

```
<210> SEQ ID NO 43
<211> LENGTH: 20
<212> TYPE: RNA
<213> ORGANISM: Homo sapiens

<400> SEQUENCE: 43
ucguuugccu uuucugcuu                                                    20

<210> SEQ ID NO 44
<211> LENGTH: 19
<212> TYPE: RNA
<213> ORGANISM: Homo sapiens

<400> SEQUENCE: 44
ggcuugcaug ggggacugg                                                    19

<210> SEQ ID NO 45
<211> LENGTH: 20
<212> TYPE: RNA
<213> ORGANISM: Homo sapiens

<400> SEQUENCE: 45
ucuuacuccc ucaggcacug                                                   20

<210> SEQ ID NO 46
<211> LENGTH: 22
<212> TYPE: RNA
<213> ORGANISM: Homo sapiens

<400> SEQUENCE: 46
ccgcacugug gguacuugcu gc                                                22

<210> SEQ ID NO 47
<211> LENGTH: 22
<212> TYPE: RNA
<213> ORGANISM: Homo sapiens

<400> SEQUENCE: 47
aggcggggcg ccgcgggacc gc                                                22

<210> SEQ ID NO 48
<211> LENGTH: 22
<212> TYPE: RNA
<213> ORGANISM: Homo sapiens

<400> SEQUENCE: 48
acugcaguga aggcacuugu ag                                                22

<210> SEQ ID NO 49
<211> LENGTH: 22
<212> TYPE: RNA
<213> ORGANISM: Homo sapiens

<400> SEQUENCE: 49
cugggagagg guuguuuacu cc                                                22

<210> SEQ ID NO 50
<211> LENGTH: 20
<212> TYPE: RNA
<213> ORGANISM: Homo sapiens

<400> SEQUENCE: 50
accaggaggc ugaggcccu                                                    20
```

-continued

```
<210> SEQ ID NO 51
<211> LENGTH: 22
<212> TYPE: RNA
<213> ORGANISM: Homo sapiens

<400> SEQUENCE: 51
aauugcacgg uauccaucug ua                                              22

<210> SEQ ID NO 52
<211> LENGTH: 20
<212> TYPE: RNA
<213> ORGANISM: Homo sapiens

<400> SEQUENCE: 52
uacaguauag augauguacu                                                 20

<210> SEQ ID NO 53
<211> LENGTH: 22
<212> TYPE: RNA
<213> ORGANISM: Homo sapiens

<400> SEQUENCE: 53
uucucaagag ggaggcaauc au                                              22

<210> SEQ ID NO 54
<211> LENGTH: 23
<212> TYPE: RNA
<213> ORGANISM: Homo sapiens

<400> SEQUENCE: 54 cgcaucccu agggcauugg ugu                                              23

<210> SEQ ID NO 55
<211> LENGTH: 22
<212> TYPE: RNA
<213> ORGANISM: Homo sapiens

<400> SEQUENCE: 55
uauugcacuu gucccggccu gu                                              22

<210> SEQ ID NO 56
<211> LENGTH: 22
<212> TYPE: RNA
<213> ORGANISM: Homo sapiens

<400> SEQUENCE: 56
uauggcacug guagaauuca cu                                              22

<210> SEQ ID NO 57
<211> LENGTH: 23
<212> TYPE: RNA
<213> ORGANISM: Homo sapiens

<400> SEQUENCE: 57
uuucaagcca gggggcguuu uuc                                             23

<210> SEQ ID NO 58
<211> LENGTH: 21
<212> TYPE: RNA
<213> ORGANISM: Homo sapiens

<400> SEQUENCE: 58
aauggcgcca cuagguugu g                                                21
```

<210> SEQ ID NO 59
<211> LENGTH: 22
<212> TYPE: RNA
<213> ORGANISM: Homo sapiens

<400> SEQUENCE: 59
ggaggggucc cgcacuggga gg                                             22

<210> SEQ ID NO 60
<211> LENGTH: 22
<212> TYPE: RNA
<213> ORGANISM: Homo sapiens

<400> SEQUENCE: 60
aaaccguuac cauuacugag uu                                             22

<210> SEQ ID NO 61
<211> LENGTH: 22
<212> TYPE: RNA
<213> ORGANISM: Homo sapiens

<400> SEQUENCE: 61
cauugcacuu gucucggucu ga                                             22

<210> SEQ ID NO 62
<211> LENGTH: 20
<212> TYPE: RNA
<213> ORGANISM: Homo sapiens

<400> SEQUENCE: 62
ucagggaguc aggggagggc                                                20

<210> SEQ ID NO 63
<211> LENGTH: 21
<212> TYPE: RNA
<213> ORGANISM: Homo sapiens

<400> SEQUENCE: 63
gugccagcug caguggggga g                                              21

<210> SEQ ID NO 64
<211> LENGTH: 21
<212> TYPE: RNA
<213> ORGANISM: Homo sapiens

<400> SEQUENCE: 64
cggcggggac ggcgauuggu c                                              21

<210> SEQ ID NO 65
<211> LENGTH: 18
<212> TYPE: RNA
<213> ORGANISM: Homo sapiens

<400> SEQUENCE: 65
cgggcguggu ggugggggg                                                 18

<210> SEQ ID NO 66
<211> LENGTH: 22
<212> TYPE: RNA
<213> ORGANISM: Homo sapiens

<400> SEQUENCE: 66
caugccuuga guguaggacc gu                                    22

<210> SEQ ID NO 67
<211> LENGTH: 22
<212> TYPE: RNA
<213> ORGANISM: Homo sapiens

<400> SEQUENCE: 67
aaggagcuca cagucuauug ag                                    22

<210> SEQ ID NO 68
<211> LENGTH: 23
<212> TYPE: RNA
<213> ORGANISM: Homo sapiens

<400> SEQUENCE: 68
uagcaccauu ugaaaucagu guu                                   23

<210> SEQ ID NO 69
<211> LENGTH: 22
<212> TYPE: RNA
<213> ORGANISM: Homo sapiens

<400> SEQUENCE: 69
ugagguagua gguuguaugg uu                                    22

<210> SEQ ID NO 70
<211> LENGTH: 23
<212> TYPE: RNA
<213> ORGANISM: Homo sapiens

<400> SEQUENCE: 70
uaaagugcuu auagugcagg uag                                   23

<210> SEQ ID NO 71
<211> LENGTH: 22
<212> TYPE: RNA
<213> ORGANISM: Homo sapiens

<400> SEQUENCE: 71
uggaguguga caauggucuu ug                                    22

<210> SEQ ID NO 72
<211> LENGTH: 22
<212> TYPE: RNA
<213> ORGANISM: Homo sapiens

<400> SEQUENCE: 72
aaaaguacuu gcggauuuug cu                                    22

<210> SEQ ID NO 73
<211> LENGTH: 21
<212> TYPE: RNA
<213> ORGANISM: Homo sapiens

<400> SEQUENCE: 73
agggagggac gggggcugug c                                     21

<210> SEQ ID NO 74
<211> LENGTH: 19
<212> TYPE: RNA
<213> ORGANISM: Homo sapiens

<400> SEQUENCE: 74
gcauugugca gggcuauca                                          19

<210> SEQ ID NO 75
<211> LENGTH: 22
<212> TYPE: RNA
<213> ORGANISM: Homo sapiens

<400> SEQUENCE: 75
cugguacagg ccuggggggac ag                                     22

<210> SEQ ID NO 76
<211> LENGTH: 22
<212> TYPE: RNA
<213> ORGANISM: Homo sapiens

<400> SEQUENCE: 76
cguguauuug acaagcugag uu                                      22

<210> SEQ ID NO 77
<211> LENGTH: 23
<212> TYPE: RNA
<213> ORGANISM: Homo sapiens

<400> SEQUENCE: 77
acugcccuaa gugcuccuuc ugg                                     23

<210> SEQ ID NO 78
<211> LENGTH: 22
<212> TYPE: RNA
<213> ORGANISM: Homo sapiens

<400> SEQUENCE: 78
ugucuuacuc ccucaggcac au                                      22

<210> SEQ ID NO 79
<211> LENGTH: 22
<212> TYPE: RNA
<213> ORGANISM: Homo sapiens

<400> SEQUENCE: 79
acccuaucaa uauugucucu gc                                      22

<210> SEQ ID NO 80
<211> LENGTH: 22
<212> TYPE: RNA
<213> ORGANISM: Homo sapiens

<400> SEQUENCE: 80
uuuggucccc uucaaccagc ua                                      22

<210> SEQ ID NO 81
<211> LENGTH: 22
<212> TYPE: RNA
<213> ORGANISM: Homo sapiens

<400> SEQUENCE: 81
cucggcgcgg ggcgcgggcu cc                                      22

<210> SEQ ID NO 82
<211> LENGTH: 24
<212> TYPE: RNA
<213> ORGANISM: Homo sapiens

```
<400> SEQUENCE: 82 ugggagcug aggcucuggg ggug                                          24

<210> SEQ ID NO 83
<211> LENGTH: 22
<212> TYPE: RNA
<213> ORGANISM: Homo sapiens

<400> SEQUENCE: 83
caaagaauuc uccuuuuggg cu                                           22

<210> SEQ ID NO 84
<211> LENGTH: 23
<212> TYPE: RNA
<213> ORGANISM: Homo sapiens

<400> SEQUENCE: 84
uuagggagua aaggguggg gag                                           23

<210> SEQ ID NO 85
<211> LENGTH: 22
<212> TYPE: RNA
<213> ORGANISM: Homo sapiens

<400> SEQUENCE: 85
uucaaguaau ccaggauagg cu                                           22

<210> SEQ ID NO 86
<211> LENGTH: 22
<212> TYPE: RNA
<213> ORGANISM: Homo sapiens

<400> SEQUENCE: 86
ugagguagga gguuguauag uu                                           22

<210> SEQ ID NO 87
<211> LENGTH: 20
<212> TYPE: RNA
<213> ORGANISM: Homo sapiens

<400> SEQUENCE: 87
cgcgggucgg ggucugcagg                                              20

<210> SEQ ID NO 88
<211> LENGTH: 22
<212> TYPE: RNA
<213> ORGANISM: Homo sapiens

<400> SEQUENCE: 88
uauugcacuc gucccggccu cc                                           22

<210> SEQ ID NO 89
<211> LENGTH: 22
<212> TYPE: RNA
<213> ORGANISM: Homo sapiens

<400> SEQUENCE: 89
uagcagcaca ucaugguuua ca                                           22

<210> SEQ ID NO 90
<211> LENGTH: 22
<212> TYPE: RNA
<213> ORGANISM: Homo sapiens
```

```
<400> SEQUENCE: 90
uggaagggag aagagcuuua au                                              22

<210> SEQ ID NO 91
<211> LENGTH: 22
<212> TYPE: RNA
<213> ORGANISM: Homo sapiens

<400> SEQUENCE: 91
ugagaacuga auuccauagg cu                                              22

<210> SEQ ID NO 92
<211> LENGTH: 17
<212> TYPE: RNA
<213> ORGANISM: Homo sapiens

<400> SEQUENCE: 92
uggagagaaa ggcagua                                                    17

<210> SEQ ID NO 93
<211> LENGTH: 22
<212> TYPE: RNA
<213> ORGANISM: Homo sapiens

<400> SEQUENCE: 93
gagcuuauuc auaaaagugc ag                                              22

<210> SEQ ID NO 94
<211> LENGTH: 23
<212> TYPE: RNA
<213> ORGANISM: Homo sapiens

<400> SEQUENCE: 94
ugagcgccuc gacgacagag ccg                                             23

<210> SEQ ID NO 95
<211> LENGTH: 22
<212> TYPE: RNA
<213> ORGANISM: Homo sapiens

<400> SEQUENCE: 95
uagcagcaca uaaugguuug ug                                              22

<210> SEQ ID NO 96
<211> LENGTH: 22
<212> TYPE: RNA
<213> ORGANISM: Homo sapiens

<400> SEQUENCE: 96
ugagguagua gguugugugg uu                                              22

<210> SEQ ID NO 97
<211> LENGTH: 21
<212> TYPE: RNA
<213> ORGANISM: Homo sapiens

<400> SEQUENCE: 97
gcgacccacu cuugguuucc a                                               21

<210> SEQ ID NO 98
<211> LENGTH: 23
<212> TYPE: RNA
```

```
<213> ORGANISM: Homo sapiens

<400> SEQUENCE: 98
ucucacacag aaaucgcacc cgu                                          23

<210> SEQ ID NO 99
<211> LENGTH: 24
<212> TYPE: RNA
<213> ORGANISM: Homo sapiens

<400> SEQUENCE: 99
aauccuugga accaggugu gagu                                          24

<210> SEQ ID NO 100
<211> LENGTH: 23
<212> TYPE: RNA
<213> ORGANISM: Homo sapiens

<400> SEQUENCE: 100
cccaguguuc agacuaccug uuc                                          23

<210> SEQ ID NO 101
<211> LENGTH: 22
<212> TYPE: RNA
<213> ORGANISM: Homo sapiens

<400> SEQUENCE: 101
ugggugguca ggagauuugu gc                                           22

<210> SEQ ID NO 102
<211> LENGTH: 23
<212> TYPE: RNA
<213> ORGANISM: Homo sapiens

<400> SEQUENCE: 102
uuuggcacua gcacauuuuu gcu                                          23

<210> SEQ ID NO 103
<211> LENGTH: 22
<212> TYPE: RNA
<213> ORGANISM: Homo sapiens

<400> SEQUENCE: 103
uguguggauc cuggaggagg ca                                           22

<210> SEQ ID NO 104
<211> LENGTH: 22
<212> TYPE: RNA
<213> ORGANISM: Homo sapiens

<400> SEQUENCE: 104
aacgccauua ucacacuaaa ua                                           22

<210> SEQ ID NO 105
<211> LENGTH: 22
<212> TYPE: RNA
<213> ORGANISM: Homo sapiens

<400> SEQUENCE: 105
uggagagaaa ggcaguuccu ga                                           22

<210> SEQ ID NO 106
<211> LENGTH: 21
```

```
<212> TYPE: RNA
<213> ORGANISM: Homo sapiens

<400> SEQUENCE: 106
uagcagcaca gaaauauugg c                                              21

<210> SEQ ID NO 107
<211> LENGTH: 22
<212> TYPE: RNA
<213> ORGANISM: Homo sapiens

<400> SEQUENCE: 107
ugaccgauuu cuccuggugu uc                                             22

<210> SEQ ID NO 108
<211> LENGTH: 21
<212> TYPE: RNA
<213> ORGANISM: Homo sapiens

<400> SEQUENCE: 108
uaccacaggg uagaaccacg g                                              21

<210> SEQ ID NO 109
<211> LENGTH: 19
<212> TYPE: RNA
<213> ORGANISM: Homo sapiens

<400> SEQUENCE: 109
uggauuuuug gaucaggga                                                 19

<210> SEQ ID NO 110
<211> LENGTH: 24
<212> TYPE: RNA
<213> ORGANISM: Homo sapiens

<400> SEQUENCE: 110
uuuggcaaug guagaacuca cacu                                           24

<210> SEQ ID NO 111
<211> LENGTH: 22
<212> TYPE: RNA
<213> ORGANISM: Homo sapiens

<400> SEQUENCE: 111
uccuucauuc caccggaguc ug                                             22

<210> SEQ ID NO 112
<211> LENGTH: 25
<212> TYPE: RNA
<213> ORGANISM: Homo sapiens

<400> SEQUENCE: 112
agggaucgcg ggcgguggc ggccu                                           25

<210> SEQ ID NO 113
<211> LENGTH: 23
<212> TYPE: RNA
<213> ORGANISM: Homo sapiens

<400> SEQUENCE: 113
gagggucuug ggagggaugu gac                                            23

<210> SEQ ID NO 114
```

```
<211> LENGTH: 23
<212> TYPE: RNA
<213> ORGANISM: Homo sapiens

<400> SEQUENCE: 114
agcagcauug uacagggcua uga                                              23

<210> SEQ ID NO 115
<211> LENGTH: 22
<212> TYPE: RNA
<213> ORGANISM: Homo sapiens

<400> SEQUENCE: 115
ugucaguuug ucaaauaccc ca                                               22

<210> SEQ ID NO 116
<211> LENGTH: 23
<212> TYPE: RNA
<213> ORGANISM: Homo sapiens

<400> SEQUENCE: 116
agcucggucu gaggccccuc agu                                              23

<210> SEQ ID NO 117
<211> LENGTH: 21
<212> TYPE: RNA
<213> ORGANISM: Homo sapiens

<400> SEQUENCE: 117
ucacagugaa ccggucucuu u                                                21

<210> SEQ ID NO 118
<211> LENGTH: 22
<212> TYPE: RNA
<213> ORGANISM: Homo sapiens

<400> SEQUENCE: 118
acaguagucu gcacauuggu ua                                               22
```

METHODS AND KITS FOR DETECTING SUBJECTS AT RISK OF HAVING CANCER

CROSS REFERENCE TO RELATED APPLICATION

This application is a U.S. National Phase of International Application No. PCT/US2012/068148, filed Dec. 6, 2012, which claims priority of U.S. Provisional Application No. 61/577,441, filed on Dec. 19, 2011. The content of these applications are incorporated herein by reference in their entirety.

FIELD OF THE INVENTION

This invention relates to methods and agents for high risk screening, early diagnosis and surveillance of cancer, in particular pancreatic cancer.

BACKGROUND OF THE INVENTION

Cancer, also known as a malignant neoplasm, refers to disorders involving unregulated cell growth. In cancer, cells divide and grow uncontrollably, forming malignant tumors, and invade nearby parts of the body. The cancer may spread to distant parts of the body through the lymphatic system or bloodstream. Despite significant advances in therapeutics and diagnostics, cancer remains a major cause of morbidity and mortality in the U.S. For some cancers, despite these advances, the incidence is on the rise.

For example, pancreatic cancer represents an aggressive tumor with less than a 5% survival rate (Jemal et al., Cancer statistics CA Cancer J. Clin. 2009; 59:225-249). Recent findings from Japan indicate that, with small tumors and no local infiltration, the survival rate can improve to over 20% (Tanaka et al. Pancreas 2004; 28(3):268-72). Survival is better upon early diagnosis. Unfortunately, the majority of pancreatic cancer patients (85%) are diagnosed at late stage as diagnosis of pancreatic cancer at an early stage has met with several challenges including lack of biomarkers suitable for early detection and associated non-cancerous pancreatic diseases, which complicate early detection. Many molecules from different classes have been interrogated as potential early detection markers, but yield no success.

Thus, there remains a need for agents and methods for high risk screening, early diagnosis and surveillance of cancer, in particular pancreatic cancer.

SUMMARY OF INVENTION

This invention relates to agents and methods for high risk screening, early diagnosis and surveillance of cancer, in particular pancreatic cancer.

Accordingly, one aspect of the invention features a method for determining whether a subject has, or is at risk of having, a cellular proliferative disorder or a method for acquiring data or information from such a subject. The method includes obtaining from the subject a sample; and determining in vitro in the sample the expression level of a microRNA, the microRNA being selected from (i) a first panel of up-regulated microRNAs or (ii) a second panel of down-regulated microRNAs. The subject or sample is classified or identified as to have, or to be at risk of having, the disorder such as pancreatic cancer if: (a) the expression level of the microRNA selected from the first panel is above a first predetermined reference value, or (b) the expression level of the microRNA selected from the second panel is below a second predetermined reference value. Examples of microRNAs of the first and second panels include those listed in Table 2. Additional examples of the first panel include miR-18a, miR-22, miR-486, miR-642b, miR-7, and miR-885-5p.

In one preferred embodiment, the method includes steps of obtaining from the subject a sample; and determining in the sample the expression level of a first microRNA. The first microRNA is selected from a panel of up-regulated microRNAs consisting of miR-18a, miR-22, miR-486, miR-642b, miR-7, and miR-885-5p. The subject or sample is classified or identified as to have, or to be at risk of having, the cellular proliferative disorder if the expression level of the first microRNA in the sample is above a predetermined reference value.

A cellular proliferative disorder refers to a disorder characterized by uncontrolled, autonomous cell growth, including non-malignant and malignant growth disorder, such as cancer or neoplastic diseases. Examples of the cellular proliferative disorder include pancreatic cancer, colon cancer, breast cancer, prostate cancer, hepatocellular carcinoma, melanoma, lung cancer, glioblastoma, brain tumor, hematopoietic malignancies, retinoblastoma, renal cell carcinoma, head and neck cancer, cervical cancer, esophageal cancer, and squamous cell carcinoma. In one embodiment, the disorder is a pancreatic cancer. In the method, the predetermined reference value can be obtained from a control subject that does not have the disorder; the subject can be one with a high risk of having the disorder. The sample can be any suitable sample, such as a body fluid sample. Examples of the body fluid include blood, serum, and plasma. In one example, the sample contains pancreatic tissue, pancreatic tumor, pancreatic cells, or pancreatic juice. The method can further include determining in the sample the expression level of a second microRNA.

In a second aspect, the invention features an array. The array includes, among others, a support having a plurality of unique locations, and any combination of (i) at least one nucleic acid having a sequence that is complementary to a microRNA selected from the above-mentioned first panel of up-regulated microRNAs or (ii) at least one nucleic acid having a sequence that is complementary to a microRNA selected from the above-mentioned second panel of down-regulated microRNAs, wherein each nucleic acid is immobilized to a unique location of the support. In a preferred embodiment, the array includes a support having a plurality of unique locations, and any combination of at least one nucleic acid having a sequence that is complementary to a microRNA selected from a panel of up-regulated microRNAs, where each nucleic acid is immobilized to a unique location of the support. The panel can include miR-18a, miR-22, miR-486, miR-642b, miR-7, and miR-885-5p. In one example, the nucleic acid is complementary to a sequence selected from the group consisting of SEQ ID NOs: 1-6. Other exemplary microRNAs include those shown in Table 2 below, where 116 miRNAs are ranked based on the significance in fold change between Pancreatic Cancer and Healthy Control or between High Risk Group and Healthy Control. Of these 116 significant mi-RNAs, at least the top 30 miRNAs showed about 2 folds or more changes (up or down) and are preferred. As shown in Table 2, the microRNAs can be grouped into two panels based on their values for "Fold Change between Pancreatic Cancer and Healthy Control." Specifically, the microRNAs in the first panel were unregulated in the pancreatic cancer patients and their "Fold Change vs Pancreatic Cancer and Healthy Control" values are greater than 1.0; the microRNAs in the second panel were down-regulated in the pancreatic cancer patients and their "Fold Change vs Pancreatic Cancer and Healthy Control" values are less than 1.0.

In a third aspect, the invention provides a kit that contains a probe having a nucleic acid sequence that is complementary to the sequence of a microRNA selected from (i) the first panel of up-regulated microRNAs or (ii) the second panel of down-regulated microRNAs or a pair of PCR primers for amplifying said microRNA. In a preferred embodiment, the nucleic acid sequence that is complementary to the sequence of microRNA selected from panel of up-regulated microRNAs or a pair of PCR primers for amplifying said microRNA. The panel can include miR-18a, miR-22, miR-486, miR-642b, miR-7, and miR-885-5p. In one example, the probe is complementary to a sequence selected from the group consisting of SEQ ID NOs: 1-6. The kit can further contain reagents for performing hybridization, reagents for performing PCR, or the above-disclosed array.

The invention also features (i) a method for determining whether a subject has, or is at risk of having, a cellular proliferative disorder, substantially as shown and described herein and (ii) an array or kit substantially as shown and described herein.

In the above methods, the identifying or classifying step can further include generating, or otherwise communicating to a third person, a report specifying that the sample or the subject has, or is at risk of having, the disorder or, for the prognosis method, that the subject under a treatment has a good or poor prognosis. In the methods mentioned above, the sample can also be a surgically or endoscopically resected pancreatic tissue sample. Examples of the sample include pancreatic tissue, pancreatic tumor, pancreatic cells, pancreatic cyst fluid, or pancreatic juice. The sample can be a body fluid sample (e.g., blood, serum, and plasma from the pancreas). In a preferred embodiment, the sample is selected from the group consisting of blood, serum, plasma, pancreatic cyst fluid, and pancreatic juice.

The details of one or more embodiments of the invention are set forth in the description below. Other features, objects, and advantages of the invention will be apparent from the description and from the claims.

BRIEF DESCRIPTION OF THE DRAWING

FIG. 1 is a diagram showing results of unsupervised cluster analysis revealed a significant (FDR<10%) and differentially regulated (>2-fold) miRNA signature comprising of 14 members that segregated pancreatic cancer patients away from not only healthy individuals but also high-risk subjects. These 14 significant microRNAs were identified from microarray experiments that probed the entire Sanger miRBASE version 16. MicroRNA probe expression values (Log 2 transformed & normalized microarray probe intensities) of selected microRNA in Cancer, High Risk and Control samples were median centered. Each column represents a single sample, and each row represents a single microRNA probe. Green squares represent lower than median levels of microRNA expression; black squares represent median levels of microRNA expression; red squares represent higher than median levels of microRNA expression. Legend units: 1.0=differs from median probe intensity by one log 2 unit (2-fold)

DETAILED DESCRIPTION OF THE INVENTION

This invention is based, at least in part, on an unexpected discovery of a number of microRNA gene products whose expression levels are altered in biological samples obtained from subjects with cancer, such as pancreatic cancer, relative to control samples. These genes can be used as biomarkers for determining whether a subject has, or is at risk of having, a cellular proliferative disorder or for determining a prognosis or surveillance of patient having such a disorder.

Accordingly, the present invention encompasses methods of diagnosing whether a subject has, or is at risk for, a cellular proliferative disorder, such as cancer or neoplastic diseases. The term "neoplastic diseases" refers to cancers of any kind and origin and precursor stages thereof. The term "neoplastic disease" includes the subject matter identified by the terms "neoplasia," "neoplasm," "cancer," "pre-cancer," or "tumor." A neoplastic disease is generally manifest by abnormal cell division resulting in an abnormal level of a particular cell population. The abnormal cell division underlying a neoplastic disease is typically inherent in the cells and not a normal physiological response to infection or inflammation. In some embodiments, neoplastic diseases for diagnosis using methods provided herein include carcinoma. By "carcinoma," it is meant a benign or malignant epithelial tumor and includes, but is not limited to, hepatocellular carcinoma, breast carcinoma, prostate carcinoma, non-small cell lung carcinoma, colon carcinoma, CNS carcinoma, melanoma, ovarian carcinoma, or renal carcinoma. An exemplary neoplastic disease is pancreatic cancer, including adenocarcinoma and neuroendocrine tumor.

The invention also provides for methods of screening subjects who are thought to be at risk for developing the above-mentioned cancer, e.g., pancreatic cancer. Also provided are methods of determining the efficacy of therapeutic regimens for inhibiting the cancer, and methods of identifying an anti-cancer agent. The invention also encompasses various kits suitable for carrying out the above mentioned methods.

MicroRNA Genes

As disclosed herein, a number of microRNA genes were identified based on their altered expression patterns in cancer patients and healthy subject. As used herein interchangeably, "microRNA," "miR," or "miRNA" refers to the unprocessed or processed RNA transcript from a miRNA gene. The unprocessed miRNA gene transcript is also called a "miRNA precursor," and typically comprises an RNA transcript of about 70-100 nucleotides in length. The miRNA precursor can be processed by digestion with an RNAse (for example, Dicer, Argonaut, or RNAse III) into an active 18-25 nucleotide RNA molecule. This active 18-25 nucleotide RNA molecule is also called the "processed" miRNA gene transcript or "mature" miRNA.

The microRNA genes of this invention can be divided into two groups. In one embodiment, the level of a miR gene product in a test sample from a patient is greater than the level of the corresponding miR gene product in a control sample (i.e., expression of the miR gene product is "up-regulated" or "over-expressed"). As used herein, expression of an miR gene product is "up-regulated" when the amount of miR gene product in a test sample from a subject is greater than the amount of the same gene product in a control sample. Examples of these up-regulated microRNAs include SEQ ID NOs:1-6 listed in Table 1 below.

TABLE 1

| S16_hsa_miRNA_name | S16_hsa_MIMAT_ID | S16_hsa_miRNA_sequence | SEQ ID NO: |
|---|---|---|---|
| hsa-miR-18a | MIMAT0000072 | UAAGGUGCAUCUAGUGCAGAUAG | 1 |
| hsa-miR-22 | MIMAT0000077 | AAGCUGCCAGUUGAAGAACUGU | 2 |
| hsa-miR-486-5p | MIMAT0002177 | UCCUGUACUGAGCUGCCCCGAG | 3 |
| hsa-miR-642b | MIMAT0018444 | AGACACAUUUGGAGAGGGACCC | 4 |
| hsa-miR-7 | MIMAT0000252 | UGGAAGACUAGUGAUUUUGUUGU | 5 |
| hsa-miR-885-5p | MIMAT0004947 | UCCAUUACACUACCCUGCCUCU | 6 |
| hsa-miR-3196 | MIMAT0015080 | CGGGGCGGCAGGGGCCUC | 7 |

These genes can be used in diagnosing cancer based on increases in their expression levels. Other up-regulated microRNAs that can be used include those described in Ho et al., Transl Oncol. 2010; 3:109-113; Wang et al. Cancer Prev Res (Phila). 2009 September; 2(9):807-13; Lee et al. Int. J. Cancer. 2007, 120(5):1046-1054; and US Application 20110171646. All of these references cited herein are incorporated herein in their entireties. The relative miR gene expression in the control samples can be determined with respect to one or more RNA expression standards. The standards can comprise, for example, the average level of miR gene expression previously obtained for a population of normal controls.

In other embodiments, the level of a target miR gene product in the test sample is less than the level of the corresponding miR gene product in the control sample (i.e., expression of the miR gene product is "down-regulated" or "under-expressed"). As used herein, expression of a miR gene is "down-regulated" when the amount of miR gene product in a test sample from a subject is less than the amount of the same gene product in a control sample.

Diagnosis and Prognosis Methods

The above-describe genes, related kits or arrays, can be used in determining whether a subject has, or is at risk of having, a cellular proliferative disorder. Alternatively, they can be used for determining a prognosis of such a disorder in a subject.

Diagnosis Methods

In one aspect, the invention provides qualitative and quantitative information to determine whether a subject has or is predisposed to a disease characterized by uncontrolled, autonomous cell growth, e.g., cancer. A subject having a cellular proliferative disorder or prone to it can be determined based on the expression levels, patterns, or profiles of the above-described genes or their products (microRNA) in a test sample from the subject. In other words, the products can be used as markers to indicate the presence or absence of the disorder. Diagnostic and prognostic assays of the invention include methods for assessing the expression level of the products. The methods and kits allow one to detect cellular proliferative disorders, such as cancer. For example, a relative increase in the expression level of one or more up-regulated genes is indicative of presence the disorder. Conversely, a lower expression level or a lack of the expression is indicative lack of the disorder.

The presence, level, or absence of the microRNA products in a test sample can be evaluated by obtaining a test sample from a test subject and contacting the test sample with a compound or an agent capable of detecting the nucleic acid (e.g., RNA or DNA probe). The "test sample" includes tissues, cells and biological fluids isolated from a subject, as well as tissues, cells and fluids present within a subject. The level of expression of a gene(s) of interest can be measured in a number of ways, including measuring the RNA encoded by the gene.

Expressed RNA samples can be isolated from biological samples using any of a number of well-known procedures. For example, biological samples can be lysed in a guanidinium-based lysis buffer, optionally containing additional components to stabilize the RNA. In some embodiments, the lysis buffer can contain purified RNAs as controls to monitor recovery and stability of RNA from cell cultures. Examples of such purified RNA templates include the Kanamycin Positive Control RNA from PROMEGA (Madison, Wis.), and 7.5 kb Poly(A)-Tailed RNA from LIFE TECHNOLOGIES (Rockville, Md.). Lysates may be used immediately or stored frozen at, e.g., −80° C.

Optionally, total RNA can be purified from cell lysates (or other types of samples) using silica-based isolation in an automation-compatible, 96-well format, such as the RNEASY purification platform (QIAGEN, Inc., Valencia, Calif.). Other RNA isolation methods are contemplated, such as extraction with silica-coated beads or guanidinium. Further methods for RNA isolation and preparation can be devised by one skilled in the art.

The methods of the present invention can be performed using crude samples (e.g., blood, serum, plasma, or cell lysates), eliminating the need to isolate RNA. RNAse inhibitors are optionally added to the crude samples. When using crude cellular lysates, it should be noted that genomic DNA can contribute one or more copies of a target sequence, e.g., a gene, depending on the sample. In situations in which the target sequence is derived from one or more highly expressed genes, the signal arising from genomic DNA may not be significant. But for genes expressed at low levels, the background can be eliminated by treating the samples with DNAse, or by using primers that target splice junctions for subsequent priming of cDNA or amplification products.

The level of RNA corresponding to a gene in a cell can be determined both in situ and in vitro. RNA isolated from a test sample can be used in hybridization or amplification assays that include, Southern or Northern analyses, PCR analyses, and probe arrays. A preferred diagnostic method for the detection of RNA levels involves contacting the isolated RNA with a nucleic acid probe that can hybridize to the RNA encoded by the gene. The probe can be a full-length nucleic acid or a portion thereof, such as an oligonucleotide of at least 10 nucleotides in length and sufficient to specifically hybridize under stringent conditions to the RNA.

In one format, RNA (or cDNA prepared from it) is immobilized on a surface and contacted with the probes, for example, by running the isolated RNA on an agarose gel and transferring the RNA from the gel to a membrane, such as nitrocellulose. In another format, the probes are immobilized on a surface and the RNA (or cDNA) is contacted with the probes, for example, in a gene chip array. A skilled artisan can adapt known RNA detection methods for detecting the level of RNA.

The level of RNA (or cDNA prepared from it) in a sample encoded by a gene to be examined can be evaluated with nucleic acid amplification, e.g., by standard PCR (U.S. Pat. No. 4,683,202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), and in situ PCR (Thaker V. Methods Mol Biol. 115:379-402, 1999), or any other nucleic acid amplification method, followed by the detection of the amplified molecules using techniques known in the art.

In another embodiment, the methods of the invention further include contacting a control sample with a compound or agent capable of detecting the RNA of a gene and comparing the presence of the RNA in the control sample with the presence of the RNA in the test sample.

The above-described methods and markers can be used to assess the risk of a subject for developing a cellular proliferative disorder, including cancer such as pancreatic cancer. In particular, the invention can be applied to those in high risk cohort who already have certain risks so as to gain critical insight into early detection. For example, approximately 10% of pancreatic cancers are hereditary in origin (Klein et al. Cancer J 2001; 7:266-73; Bartsch et al. Int J Cancer 2004; 110:902-6; and Hemminki et al. Int J Cancer 2003; 103:525-30) and in some individuals the lifetime risk of pancreatic cancer approaches 50% (Rulyak et al. Pancreatology 2001; 1(5):477-85), a microRNA signature for screening and surveillance would be significant.

As used herein "one with a high risk of having pancreatic cancer" to include individuals who meet one or more of the following criteria.

1. Individuals with two or more first degree relatives with pancreatic cancer;
2. Individuals with one first degree relative diagnosed with pancreatic cancer at an early age (under the age of 50);
3. Individuals with two or more second degree relatives with pancreatic cancer, one of whom developed it at an early age (under the age of 60);
4. Members of families affected by BRCA I and BRCA II mutations;
5. Members of families with familial atypical multiple-mole melanoma (FAMM) syndromes;
6. Having heredity pancreatitis;
7. Having HNPCC Syndrome;
8. Having Familial Adenomatous Polyposis (FAP) Syndrome;
9. Having Peutz-Jeghers Syndrome; and
10. Patients who have been found with abnormal ultrasonography or CT imaging of the pancreas through routine examinations with conventional method.

A change in levels of miR gene products associated with pancreatic cancer can be detected prior to, or in the early stages of, the development of transformed or neoplastic phenotypes in cells of a subject. The invention therefore also provides a method for screening a subject who is at risk of developing pancreatic cancer, comprising evaluating the level of at least one miR gene product, or a combination of miR gene products, associated with pancreatic cancer in a biological sample obtained form the subject's pancreas. Accordingly, an alteration in the level of the miR gene product, or combination of miR gene products, in the biological sample as compared to the level of a corresponding miR gene product in a control sample, is indicative of the subject being at risk for developing pancreatic cancer. The biological sample used for such screening can include pancreatic tissue that is either normal or suspected to be precancerous. Subjects with a change in the level of one or more miR gene products associated with pancreatic cancer are candidates for further monitoring and testing. Such further testing can comprise histological examination of tissue samples, or other techniques within the skill in the art.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder, e.g., pancreatic cancer.

Prognosis Methods

The diagnostic methods described above can identify subjects having, or at risk of developing, a disease or disorder associated with cellular proliferative disorder. In addition, changes in expression levels and/or trends of the above-mentioned genes (or a subset of it) in a biological sample, e.g., peripheral blood samples, can provide an early indication of recovery or lack thereof. For example, a further increase (or decline) or persistently-altered gene expression levels of the unregulated genes (or down-regulated genes) indicate a poor prognosis, i.e., lack of improvement or health decline. Accordingly, these genes allow one to assess post-treatment recovery of cancer. The analysis of this select group of genes or a subset thereof indicates outcomes of the conditions.

The prognostic assays described herein can be used to determine whether a subject is suitable to be administered with an agent (e.g., an agonist, antagonist, peptidomimetic, protein, peptide, nucleic acid, small molecule, or other drug candidate) to treat a disorder associated with uncontrolled, autonomous cell growth. For example, such assays can be used to determine whether a subject can be administered with a chemotherapeutic agent Thus, also provided by this invention is a method of monitoring a treatment for a cellular proliferative disorder in a subject. For this purpose, gene expression levels of the genes disclosed herein can be determined for test samples from a subject before, during, or after undergoing a treatment. The magnitudes of the changes in the levels as compared to a baseline level are then assessed. A decrease of the magnitudes of the changes after the treatment indicates that the subject can be further treated by the same treatment. For example, a relative decrease in the expression level of one or more up-regulated genes is indicative of recovery from the disorder. Conversely, further increase or persistent high expression levels of one or more of the up-regulated genes is indicate lack of improvement or health decline.

Information obtained from practice of the above assays is useful in prognostication, identifying progression of, and clinical management of diseases and other deleterious conditions affecting an individual subject's health status. In preferred embodiments, the foregoing diagnostic assays provide information useful in prognostication, identifying progression of and management of conditions that are characterized by uncontrolled, autonomous cell growth. The information more specifically assists the clinician in designing chemotherapeutic or other treatment regimes to eradicate such conditions from the body of an afflicted subject, a human.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, a positive prognosis is one where a patient has a 50% probability of being cured of a particular cancer after treatment, while the average patient with the same cancer has only a 25% probability of being cured.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" a target includes determining the amount of the target present, as well as determining whether it is present or absent.

Arrays

Also provided in the invention is a biochip or array. The biochip/array may contain a solid or semi-solid substrate having an attached probe or plurality of probes described herein. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

"Attached" or "immobilized" as used herein to refer to a nucleic acid (e.g., a probe) and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

The solid substrate can be a material that may be modified to contain discrete individual sites appropriate for the attachment or association of the probes and is amenable to at least one detection method. Examples of such substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate can be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The array/biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide. The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography. Detailed discussion of methods for linking nucleic acids to a support substrate can be found in, e.g., U.S. Pat. Nos. 5,837,832, 6,087,112, 5215882, 5707807, 5807522, 5958342, 5994076, 6004755, 6048695, 6060240, 6090556, and 6040138.

In some embodiments, an expressed transcript (e.g., a transcript of a microRNA gene described herein) is represented in the nucleic acid arrays. In such embodiments, a set of binding sites can include probes with different nucleic acids that are complementary to different sequence segments of the expressed transcript. Examples of such nucleic acids can be of length of 15 to 200 bases, 20 to 100 bases, 25 to 50 bases, 40 to 60 bases. Each probe sequence can also include one or more linker sequences in addition to the sequence that is complementary to its target sequence. A linker sequence is a sequence between the sequence that is complementary to its target sequence and the surface of support. For example, the nucleic acid arrays of the invention can have one probe specific to each target microRNA gene. However, if desired, the nucleic acid arrays can contain at least 2, 5, 10, 100, 200, 300, 400, 500 or more probes specific to some expressed transcript (e.g., a transcript of a microRNA gene described herein, e.g., SEQ ID NOs: 1-6).

Kits

In another aspect, the present invention provides kits embodying the methods, compositions, and systems for analysis of microRNA gene expression as described herein.

Such a kit may contain a nucleic acid described herein together with any or all of the following: assay reagents, buffers, probes and/or primers, and sterile saline or another pharmaceutically acceptable emulsion and suspension base. In addition, the kit may include instructional materials containing directions (e.g., protocols) for the practice of the methods described herein. For example, the kit may be a kit for the amplification, detection, identification or quantification of a target microRNA sequence. To that end, the kit may contain a suitable primer (e.g., hairpin primers), a forward primer, a reverse primer, and a probe.

In one example, a kit of the invention includes one or more microarray slides (or alternative microarray format) onto which a plurality of different nucleic acids (each corresponding to one of the above-mentioned genes) have been deposited. The kit can also include a plurality of labeled probes. Alternatively, the kit can include a plurality of polynucleotide sequences suitable as probes and a selection of labels suitable for customizing the included polynucleotide sequences, or other polynucleotide sequences at the discretion of the practitioner. Commonly, at least one included polynucleotide sequence corresponds to a control sequence, e.g., a normalization gene or the like. Exemplary labels include, but are not limited to, a fluorophore, a dye, a radiolabel, an enzyme tag, that is linked to a nucleic acid primer.

In one embodiment, kits that are suitable for amplifying nucleic acid corresponding to the expressed RNA samples are provided. Such a kit includes reagents and primers suitable for use in any of the amplification methods described above. Alternatively, or additionally, the kits are suitable for amplifying a signal corresponding to hybridization between a probe and a target nucleic acid sample (e.g., deposited on a microarray).

In addition, one or more materials and/or reagents required for preparing a biological sample for gene expression analysis are optionally included in the kit. Furthermore, optionally included in the kits are one or more enzymes suitable for amplifying nucleic acids, including various polymerases (RT, Taq, etc.), one or more deoxynucleotides, and buffers to provide the necessary reaction mixture for amplification.

Typically, the kits are employed for analyzing gene expression patterns using microRNA as the starting template. The mRNA template may be presented as either total cellular RNA or isolated microRNA; both types of sample yield comparable results. In other embodiments, the methods and kits described in the present invention allow quantitation of other products of gene expression, including tRNA, rRNA, or other transcription products.

Optionally, the kits of the invention further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

The kits optionally contain distinct containers for each individual reagent and/or enzyme component. Each component will generally be suitable as aliquoted in its respective container. The container of the kits optionally includes at least one vial, ampule, or test tube. Flasks, bottles and other container mechanisms into which the reagents can be placed and/or aliquoted are also possible. The individual containers of the kit are preferably maintained in close confinement for commercial sale. Suitable larger containers may include injection or blow-molded plastic containers into which the desired vials are retained. Instructions, such as written directions or videotaped demonstrations detailing the use of the kits of the present invention, are optionally provided with the kit.

In a further aspect, the present invention provides for the use of any composition or kit herein, for the practice of any method or assay herein, and/or for the use of any apparatus or kit to practice any assay or method herein.

A "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model.

A "test sample" or a "biological sample" as used herein may mean a sample of biological tissue or fluid that comprises nucleic acids. Such samples include, but are not limited to, tissue or body fluid isolated from animals. Biological samples may also include sections of tissues such as biopsy and autopsy samples, frozen sections taken for histological purposes, blood, plasma, serum, sputum, stool, tears, mucus, urine, effusions, amniotic fluid, ascitic fluid, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

The term "body fluid" or "bodily fluid" refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample: for example, the sample may be frozen at about −20° C. to about −70° C. Suitable body fluids are acellular fluids. "Acellular" fluids include body fluid samples in which cells are absent or are present in such low amounts that the miRNA level determined reflects its level in the liquid portion of the sample, rather than in the cellular portion. Such acellular body fluids are generally produced by processing a cell-containing body fluid by, for example, centrifugation or filtration, to remove the cells. Typically, an acellular body fluid contains no intact cells however, some may contain cell fragments or cellular debris. Examples of acellular fluids include plasma or serum, or body fluids from which cells have been removed.

The term "gene" used herein refers to a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto. The term also includes pseudogenes, which are dysfunctional relatives of known genes that have lost their protein-coding ability or are otherwise no longer expressed in a cell.

"Expression profile" refers to a genomic expression profile, e.g., an expression profile of microRNAs. Profiles may be generated by any convenient means for determining a level of a nucleic acid sequence e.g., quantitative hybridization of microRNA, cRNA, etc., quantitative PCR, ELISA for quantification, and the like, and allow the analysis of differential gene expression between two samples. A subject or patient sample, e.g., cells or a collection thereof, e.g., tissues, is assayed. Samples are collected by any convenient method known in the art. Nucleic acid sequences of interest are nucleic acid sequences that are found to be predictive, including the nucleic acid sequences of those described herein, where the expression profile may include expression data for 5, 10, 20, 25, 50, 100 or more of, including all of the listed nucleic acid sequences. The term "expression profile" may also mean measuring the abundance of the nucleic acid sequences in the measured samples.

"Differential expression" refers to qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state, relative to another state thus permitting comparison of two or more states. A qualitatively regulated gene will exhibit an expression pattern within a state or cell type that may be detectable by standard techniques. Some genes will be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, Northern analysis, and RNase protection.

"Nucleic acid" or "oligonucleotide" or "polynucleotide" as used herein refers to at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

The term "primer" refers to any nucleic acid that is capable of hybridizing at its 3' end to a complementary nucleic acid molecule, and that provides a free 3' hydroxyl terminus which can be extended by a nucleic acid polymerase. As used herein, amplification primers are a pair of nucleic acid molecules that can anneal to 5' or 3' regions of a gene (plus and minus strands, respectively, or vice-versa) and contain a short region in between. Under appropriate conditions and with appropriate reagents, such primers permit the amplification of a nucleic acid molecule having the nucleotide sequence flanked by the primers. For in situ methods, a cell or tissue sample can be prepared and immobilized on a support, such as a glass slide, and then contacted with a probe that can hybridize to RNA. Alternative methods for amplifying nucleic acids corresponding to expressed RNA samples include those described in, e.g., U.S. Pat. No. 7,897,750.

The term "probe" as used herein refers to an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

"Stringent hybridization conditions" as used herein refers to conditions under which a first nucleic acid sequence (e.g., probe) hybridizes to a second nucleic acid sequence (e.g., target), such as in a complex mixture of nucleic acids. Stringent conditions are sequence-dependent and be different in different circumstances, and can be suitably selected by one skilled in the art. Stringent conditions may be selected to be about 5-10° C. lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C. However, several factors other than temperature, such as salt concentration, can influence the stringency of hybridization and one skilled in the art can suitably select the factors to accomplish a similar stringency.

As used herein the term "reference value" refers to a value that statistically correlates to a particular outcome when compared to an assay result. In preferred embodiments, the reference value is determined from statistical analysis of studies that compare microRNA expression with known clinical outcomes. The reference value may be a threshold score value or a cutoff score value. Typically a reference value will be a threshold above (or below) which one outcome is more probable and below which an alternative threshold is more probable.

In one embodiment, a reference level may be one or more circulating miRNA levels expressed as an average of the level of the circulating miRNA from samples taken from a control population of healthy (disease-free) subjects. In another embodiment, the reference level may be the level in the same subject at a different time, e.g., before the present assay, such as the level determined prior to the subject developing the disease or prior to initiating therapy. In general, samples are normalized by a common factor. For example, acellular body fluid samples are normalized by volume body fluid and cell-containing samples are normalized by protein content or cell count. Nucleic acid samples may also be normalized relative to an internal control nucleic acid.

As disclosed herein, the difference of the level of one or more microRNAs is indicative of a disease or a stage thereof. The phrase "difference of the level" refers to differences in the quantity of a particular marker, such as a nucleic acid, in a sample as compared to a control or reference level. For example, the quantity of a particular biomarker may be present at an elevated amount or at a decreased amount in samples of patients with a neoplastic disease compared to a reference level. In one embodiment, a "difference of a level" may be a difference between the quantity of a particular biomarker present in a sample as compared to a control (e.g., reference value) of at least about 1%, 2%, 3%, 5%, 10%, 15%, 20%, 25%, 30%, 35%, 40%, 50%, 60%, 75%, 80% 100%, 150%, 200%, or more. In one embodiment, a "difference of a level" may be a statistically significant difference between the quantities of a biomarker present in a sample as compared to a control. For example, a difference may be statistically significant if the measured level of the biomarker falls outside of about 1.0 standard deviation, about 1.5 standard deviations, about 2.0 standard deviations, or about 2.5 stand deviations of the mean of any control or reference group. With respect to miRNA measurement, the level may be measured from real-time PCR as the Ct value, which may be normalized to a $\Delta$Ct value as described in the Examples below.

EXAMPLE 1

In this example, microRNA microarray screening was conducted to identify microRNAs whose expression levels were altered in pancreatic cancer patients.

Briefly, total RNAs were isolated from serum samples of 30 humans and subjected to global miRNA profiling using microarray that was designed to sample the current miRNA sequence information available to date, Sanger miRBase Release 16 (http://www.mirbase.org/cgi-bin/mirna_summary.pl?org=hsa). The microarray was designed to detect close to 1000 human miRNA sequences. The serum samples were derived from 10 healthy subject, 10 pancreatic cancer patients (including 9 having Stage 2A/2B pancreatic cancer and 1 having neuroendocrine tumor), and 10 high risk subjects.

More specifically, 2,576 human miRNA were screening. It was found that about 290 human serum miRNAs showed high intensity and met the cutoff threshold value. Among them, 116 miRNAs were identified as significant microRNA signatures for pancreatic cancer blood plasma. See Table 2 below, where the 116 miRNA are ranked based on the significance in fold change between Pancreatic Cancer and Healthy Control or between High Risk Group and Healthy Control. Of these 116 significant mi-RNAs, at least the top 30 miRNAs showed about 2 folds or more changes (up or down).

Furthermore, as shown in Table 2, the microRNAs can be grouped into two panels based on their values for "Fold Change between Pancreatic Cancer and Healthy Control." Specifically, the microRNAs in the first panel were unregulated in the pancreatic cancer patients and their "Fold Change vs Pancreatic Cancer and Healthy Control" values are greater than 1.0; the microRNAs in the second panel were down-regulated in the pancreatic cancer patients and their "Fold Change vs Pancreatic Cancer and Healthy Control" values are less than 1.0.

Unsupervised clustering using 16 miRNAs (based on fold and p value) illustrated that the majority (8/9) of pancreatic cancer subjects segregated from healthy subjects. See FIG. 1. It was also found that the single pancreatic neuroendocrine tumor segregated within the cluster of healthy subjects.

Furthermore, a candidate miRNA signature of 12 individual miRNAs was identified as being able to distinguish pancreatic cancer subjects from healthy subjects. This signature was identified based the criteria shown below in pancreatic cancer subjects as compared to healthy subjects: (i) Up-regulated >3.1-fold, (ii) p-value <0.005, (iii) Sensitivity: >77% for detecting the cancer subjects, and (iv) Specificity: >70% for detecting healthy subjects based on preliminary receiver operating characteristic (ROC) analysis. This candidate miRNA signature of 12 individual miRNAs differs from miRNAs previously reported in Bloomston et al., JAMA 2007; 297:1901-8; Szafranska et al., Oncogene 2007; 26:4442-52; Szafranska et al., Clin Chem. 2008; 54:1716-24; and Lee et al., Int J. Cancer. 2007; 120:1046-54. Those miRNAs described in the articles were identified from microarray analyses of pancreatic cancer biopsies of end-stage subjects using probes designed to detect fewer numbers of microRNAs based on early releases of miRBase.

TABLE 2

| S16_hsa_miRNA_name | S16_hsa_MIMAT_ID | SEQ ID NO: | S16_hsa_miRNA_sequence |
|---|---|---|---|
| hsa-miR-3184 | MIMAT0015064 | 8 | UGAGGGGCCUCAGACCGAGCUUUU |
| hsa-miR-642b | MIMAT0018444 | 4 | AGACACAUUUGGAGAGGGACCC |
| hsa-miR-1909 | MIMAT0007883 | 9 | CGCAGGGGCCGGGUGCUCACCG |
| hsa-miR-486-5p | MIMAT0002177 | 3 | UCCUGUACUGAGCUGCCCCGAG |
| hsa-miR-711 | MIMAT0012734 | 10 | GGGACCCAGGGAGAGACGUAAG |
| hsa-miR-3125 | MIMAT0014988 | 11 | UAGAGGAAGCUGUGGAGAGA |
| hsa-miR-18b | MIMAT0001412 | 12 | UAAGGUGCAUCUAGUGCAGAUAG |
| hsa-miR-762 | MIMAT0010313 | 13 | GGGGCUGGGGCCGGGGCCGAGC |
| hsa-miR-3154 | MIMAT0015028 | 14 | CAGAAGGGGAGUUGGGAGCAGA |
| hsa-miR-486-3p | MIMAT0004762 | 15 | CGGGGCAGCUCAGUACAGGAU |
| hsa-miR-18a | MIMAT0000072 | 1 | UAAGGUGCAUCUAGUGCAGAUAG |
| hsa-miR-4253 | MIMAT0016882 | 16 | AGGGCAUGUCCAGGGGU |
| hsa-miR-1288 | MIMAT0005942 | 17 | UGGACUGCCCUGAUCUGGAGA |
| hsa-miR-885-5p | MIMAT0004947 | 6 | UCCAUUACACUACCCUGCCUCU |
| hsa-miR-7 | MIMAT0000252 | 5 | UGGAAGACUAGUGAUUUUGUUGU |
| hsa-miR-26b | MIMAT0000083 | 18 | UUCAAGUAAUUCAGGAUAGGU |
| hsa-miR-301a | MIMAT0000688 | 19 | CAGUGCAAUAGUAUUGUCAAAGC |
| hsa-miR-106b | MIMAT0000680 | 20 | UAAAGUGCUGACAGUGCAGAU |
| hsa-miR-646 | MIMAT0003316 | 21 | AAGCAGCUGCCUCUGAGGC |
| hsa-miR-1295 | MIMAT0005885 | 22 | UUAGGCCGCAGAUCUGGGUGA |
| hsa-miR-20b | MIMAT0001413 | 23 | CAAAGUGCUCAUAGUGCAGGUAG |
| hsa-miR-93 | MIMAT0000093 | 24 | CAAAGUGCUGUUCGUGCAGGUAG |
| hsa-miR-16 | MIMAT0000069 | 25 | UAGCAGCACGUAAAUAUUGGCG |
| hsa-miR-3188 | MIMAT0015070 | 26 | AGAGGCUUUGUGCGGAUACGGGG |
| hsa-miR-106a | MIMAT0000103 | 27 | AAAAGUGCUUACAGUGCAGGUAG |
| hsa-miR-17 | MIMAT0000070 | 28 | CAAAGUGCUUACAGUGCAGGUAG |
| hsa-miR-1468 | MIMAT0006789 | 29 | CUCCGUUUGCCUGUUUCGCUG |
| hsa-miR-19b | MIMAT0000074 | 30 | UGUGCAAAUCCAUGCAAAACUGA |
| hsa-miR-193b | MIMAT0002819 | 31 | AACUGGCCCUCAAAGUCCCGCU |
| hsa-miR-194 | MIMAT0000460 | 32 | UGUAACAGCAACUCCAUGUGGA |
| hsa-miR-150 | MIMAT0000451 | 33 | UCUCCCAACCCUUGUACCAGUG |
| hsa-miR-16-2* | MIMAT0004518 | 34 | CCAAUAUUACUGUGCUGCUUUA |
| hsa-let-7g | MIMAT0000414 | 35 | UGAGGUAGUAGUUUGUACAGUU |
| hsa-miR-103-2* | MIMAT0009196 | 36 | AGCUUCUUUACAGUGCUGCCUUG |
| hsa-miR-3937 | MIMAT0018352 | 37 | ACAGGCGGCUGUAGCAAUGGGG |
| hsa-miR-548o | MIMAT0005919 | 38 | CCAAAACUGCAGUUACUUUUGC |

TABLE 2-continued

| | | | |
|---|---|---|---|
| hsa-let-7i | MIMAT0000415 | 39 | UGAGGUAGUAGUUUGUGCUGUU |
| hsa-miR-373* | MIMAT0000725 | 40 | ACUCAAAAUGGGGGCGCUUUCC |
| hsa-miR-484 | MIMAT0002174 | 41 | UCAGGCUCAGUCCCUCCCGAU |
| hsa-miR-338-3p | MIMAT0000763 | 42 | UCCAGCAUCAGUGAUUUUGUUG |
| hsa-miR-1282 | MIMAT0005940 | 43 | UCGUUUGCCUUUUUCUGCUU |
| hsa-miR-4327 | MIMAT0016889 | 44 | GGCUUGCAUGGGGGACUGG |
| hsa-miR-550b | MIMAT0018445 | 45 | UCUUACUCCCUCAGGCACUG |
| hsa-miR-106b* | MIMAT0004672 | 46 | CCGCACUGUGGGUACUUGCUGC |
| hsa-miR-663 | MIMAT0003326 | 47 | AGGCGGGGCGCCGCGGGACCGC |
| hsa-miR-17* | MIMAT0000071 | 48 | ACUGCAGUGAAGGCACUUGUAG |
| hsa-miR-30c-1* | MIMAT0004674 | 49 | CUGGGAGAGGGUUGUUUACUCC |
| hsa-miR-665 | MIMAT0004952 | 50 | ACCAGGAGGCUGAGGCCCCU |
| hsa-miR-363 | MIMAT0000707 | 51 | AAUUGCACGGUAUCCAUCUGUA |
| hsa-miR-144 | MIMAT0000436 | 52 | UACAGUAUAGAUGAUGUACU |
| hsa-miR-514b-5p | MIMAT0015087 | 53 | UUCUCAAGAGGGAGGCAAUCAU |
| hsa-miR-324-5p | MIMAT0000761 | 54 | CGCAUCCCCUAGGGCAUUGGUGU |
| hsa-miR-92a | MIMAT0000092 | 55 | UAUUGCACUUGUCCCGGCCUGU |
| hsa-miR-183 | MIMAT0000261 | 56 | UAUGGCACUGGUAGAAUUCACU |
| hsa-miR-498 | MIMAT0002824 | 57 | UUUCAAGCCAGGGGGCGUUUUUC |
| hsa-miR-652 | MIMAT0003322 | 58 | AAUGGCGCCACUAGGGUUGUG |
| hsa-miR-1914* | MIMAT0007890 | 59 | GGAGGGGUCCCGCACUGGGAGG |
| hsa-miR-451 | MIMAT0001631 | 60 | AAACCGUUACCAUUACUGAGUU |
| hsa-miR-25 | MIMAT0000081 | 61 | CAUUGCACUUGUCUCGGUCUGA |
| hsa-miR-4270 | MIMAT0016900 | 62 | UCAGGGAGUCAGGGGAGGGC |
| hsa-miR-1202 | MIMAT0005865 | 63 | GUGCCAGCUGCAGUGGGGGAG |
| hsa-miR-1908 | MIMAT0007881 | 64 | CGGCGGGGACGGCGAUUGGUC |
| hsa-miR-1268 | MIMAT0005922 | 65 | CGGGCGUGGUGGUGGGGG |
| hsa-miR-532-5p | MIMAT0002888 | 66 | CAUGCCUUGAGUGUAGGACCGU |
| hsa-miR-28-5p | MIMAT0000085 | 67 | AAGGAGCUCACAGUCUAUUGAG |
| hsa-miR-29b | MIMAT0000100 | 68 | UAGCACCAUUUGAAAUCAGUGUU |
| hsa-let-7c | MIMAT0000064 | 69 | UGAGGUAGUAGGUUGUAUGGUU |
| hsa-miR-20a | MIMAT0000075 | 70 | UAAAGUGCUUAUAGUGCAGGUAG |
| hsa-miR-122 | MIMAT0000421 | 71 | UGGAGUGUGACAAUGGUGUUUG |
| hsa-miR-548k | MIMAT0005882 | 72 | AAAAGUACUUGCGGAUUUUGCU |
| hsa-miR-149* | MIMAT0004609 | 73 | AGGGAGGGACGGGGGCUGUGC |
| hsa-miR-4289 | MIMAT0016920 | 74 | GCAUUGUGCAGGGCUAUCA |
| hsa-miR-150* | MIMAT0004610 | 75 | CUGGUACAGGCCUGGGGGACAG |

TABLE 2-continued

| Name | Accession | SEQ ID NO | Sequence |
|---|---|---|---|
| hsa-miR-223* | MIMAT0004570 | 76 | CGUGUAUUUGACAAGCUGAGUU |
| hsa-miR-18a* | MIMAT0002891 | 77 | ACUGCCCUAAGUGCUCCUUCUGG |
| hsa-miR-550a* | MIMAT0003257 | 78 | UGUCUUACUCCCUCAGGCACAU |
| hsa-miR-454* | MIMAT0003884 | 79 | ACCCUAUCAAUAUUGUCUCUGC |
| hsa-miR-133b | MIMAT0000770 | 80 | UUUGGUCCCCUUCAACCAGCUA |
| hsa-miR-1469 | MIMAT0007347 | 81 | CUCGGCGCGGGCGCGGGCUCC |
| hsa-miR-939 | MIMAT0004982 | 82 | UGGGGAGCUGAGGCUCUGGGGGUG |
| hsa-miR-186 | MIMAT0000456 | 83 | CAAAGAAUUCUCCUUUUGGGCU |
| hsa-miR-3162 | MIMAT0015036 | 84 | UUAGGGAGUAGAAGGGUGGGGAG |
| hsa-miR-26a | MIMAT0000082 | 85 | UUCAAGUAAUCCAGGAUAGGCU |
| hsa-let-7e | MIMAT0000066 | 86 | UGAGGUAGGAGGUUGUAUAGUU |
| hsa-miR-3621 | MIMAT0018002 | 87 | CGCGGGUCGGGUCUGCAGG |
| hsa-miR-92b | MIMAT0003218 | 88 | UAUUGCACUCGUCCCGGCCUCC |
| hsa-miR-15b | MIMAT0000417 | 89 | UAGCAGCACAUCAUGGUUUACA |
| hsa-miR-3202 | MIMAT0015089 | 90 | UGGAAGGGAGAAGAGCUUUAAU |
| hsa-miR-146b-5p | MIMAT0002809 | 91 | UGAGAACUGAAUUCCAUAGGCU |
| hsa-miR-4306 | MIMAT0016858 | 92 | UGGAGAGAAAGGCAGUA |
| hsa-miR-590-5p | MIMAT0003258 | 93 | GAGCUUAUUCAUAAAAGUGCAG |
| hsa-miR-339-3p | MIMAT0004702 | 94 | UGAGCGCCUCGACGACAGAGCCG |
| hsa-miR-15a | MIMAT0000068 | 95 | UAGCAGCACAUAAUGGUUUGUG |
| hsa-let-7b | MIMAT0000063 | 96 | UGAGGUAGUAGGUUGUGUGGUU |
| hsa-miR-551a | MIMAT0003214 | 97 | GCGACCCACUCUUGGUUUCCA |
| hsa-miR-342-3p | MIMAT0000753 | 98 | UCUCACACAGAAAUCGCACCCGU |
| hsa-miR-362-5p | MIMAT0000705 | 99 | AAUCCUUGGAACCUAGGUGUGAGU |
| hsa-miR-199a-5p | MIMAT0000231 | 100 | CCCAGUGUUCAGACUACCUGUUC |
| hsa-miR-1293 | MIMAT0005883 | 101 | UGGGUGGUCUGGAGAUUUGUGC |
| hsa-miR-96 | MIMAT0000095 | 102 | UUUGGCACUAGCACAUUUUUGCU |
| hsa-miR-3911 | MIMAT0018185 | 103 | UGUGUGGAUCCUGGAGGAGGCA |
| hsa-miR-122* | MIMAT0004590 | 104 | AACGCCAUUAUCACACUAAAUA |
| hsa-miR-185 | MIMAT0000455 | 105 | UGGAGAGAAAGGCAGUUCCUGA |
| hsa-miR-195 | MIMAT0000461 | 106 | UAGCAGCACAGAAAUAUUGGC |
| hsa-miR-29c* | MIMAT0004673 | 107 | UGACCGAUUUCUCCUGGUGUUC |
| hsa-miR-140-3p | MIMAT0004597 | 108 | UACCACAGGGUAGAACCACGG |
| hsa-miR-1290 | MIMAT0005880 | 109 | UGGAUUUUUGGAUCAGGGA |
| hsa-miR-182 | MIMAT0000259 | 110 | UUUGGCAAUGGUAGAACUCACACU |
| hsa-miR-205 | MIMAT0000266 | 111 | UCCUUCAUUCCACCGGAGUCUG |

TABLE 2-continued

| | | | |
|---|---|---|---|
| hsa-miR-638 | MIMAT0003308 | 112 | AGGGAUCGCGGGCGGGUGGCGGCCU |
| hsa-miR-1182 | MIMAT0005827 | 113 | GAGGGUCUUGGGAGGGAUGUGAC |
| hsa-miR-103 | MIMAT0000101 | 114 | AGCAGCAUUGUACAGGGCUAUGA |
| hsa-miR-223 | MIMAT0000280 | 115 | UGUCAGUUUGUCAAAUACCCCA |
| hsa-miR-423-3p | MIMAT0001340 | 116 | AGCUCGGUCUGAGGCCCCUCAGU |
| hsa-miR-128 | MIMAT0000424 | 117 | UCACAGUGAACCGGUCUCUUU |
| hsa-miR-199a-3p;hsa-miR-199b-3p | MIMAT0000232; MIMAT0004563 | 118 | ACAGUAGUCUGCACAUUGGUUA |

| S16_hsa_miRNA_name | Fold Change Pancreatic Cancer vs Healthy Control | Fold Change High Risk Group vs Healthy Control | P | FDR | rank |
|---|---|---|---|---|---|
| hsa-miR-3184 | 3.76 | 0.60 | 0.00E+00 | 1.00E-03 | 1 |
| hsa-miR-642b | 2.91 | 0.90 | 6.00E-05 | 6.80E-03 | 2 |
| hsa-miR-1909 | 2.76 | 0.69 | 7.00E-05 | 6.80E-03 | 3 |
| hsa-miR-486-5p | 0.37 | 1.06 | 2.70E-04 | 1.77E-02 | 4 |
| hsa-miR-711 | 2.61 | 0.64 | 3.00E-04 | 1.77E-02 | 5 |
| hsa-miR-3125 | 3.91 | | 4.40E-04 | 2.13E-02 | 6 |
| hsa-miR-18b | 0.38 | 1.57 | 5.10E-04 | 2.13E-02 | 7 |
| hsa-miR-762 | 2.24 | 0.78 | 7.40E-04 | 2.36E-02 | 8 |
| hsa-miR-3154 | 3.36 | 0.87 | 7.80E-04 | 2.36E-02 | 9 |
| hsa-miR-486-3p | | 1.10 | 8.10E-04 | 2.36E-02 | 10 |
| hsa-miR-18a | 0.41 | 1.59 | 9.70E-04 | 2.56E-02 | 11 |
| hsa-miR-4253 | 2.57 | 0.97 | 1.09E-03 | 2.58E-02 | 12 |
| hsa-miR-1288 | 0.43 | 0.05 | 1.23E-03 | 2.58E-02 | 13 |
| hsa-miR-885-5p | 2.52 | 0.62 | 1.27E-03 | 2.58E-02 | 14 |
| hsa-miR-7 | | 0.78 | 1.34E-03 | 2.58E-02 | 15 |
| hsa-miR-26b | 0.32 | 1.75 | 1.83E-03 | 3.32E-02 | 16 |
| hsa-miR-301a | 0.46 | 1.63 | 2.03E-03 | 3.47E-02 | 17 |
| hsa-miR-106b | 0.47 | 1.69 | 2.83E-03 | 4.24E-02 | 18 |
| hsa-miR-646 | 0.45 | 0.54 | 2.84E-03 | 4.24E-02 | 19 |
| hsa-miR-1295 | 0.46 | 0.48 | 2.93E-03 | 4.24E-02 | 20 |
| hsa-miR-20b | 0.39 | 1.97 | 4.34E-03 | 5.59E-02 | 21 |
| hsa-miR-93 | 0.45 | 1.98 | 4.44E-03 | 5.59E-02 | 22 |
| hsa-miR-16 | 0.34 | 0.61 | 4.60E-03 | 5.59E-02 | 23 |
| hsa-miR-3188 | 2.25 | 0.84 | 4.64E-03 | 5.59E-02 | 24 |
| hsa-miR-106a | 0.44 | 2.47 | 5.63E-03 | 5.59E-02 | 25 |
| hsa-miR-17 | 0.45 | 2.56 | 5.74E-03 | 5.59E-02 | 26 |
| hsa-miR-1468 | 0.49 | 0.12 | 5.74E-03 | 5.59E-02 | 27 |

TABLE 2-continued

| | | | | | |
|---|---|---|---|---|---|
| hsa-miR-19b | 0.46 | 1.08 | 5.80E-03 | 5.59E-02 | 28 |
| hsa-miR-193b | 2.07 | 0.77 | 6.22E-03 | 5.59E-02 | 29 |
| hsa-miR-194 | 1.97 | 1.11 | 6.22E-03 | 5.59E-02 | 30 |
| hsa-miR-150 | 0.48 | 2.01 | 6.25E-03 | 5.59E-02 | 31 |
| hsa-miR-16-2* | 0.48 | 0.98 | 6.35E-03 | 5.59E-02 | 32 |
| hsa-let-7g | 0.33 | 2.91 | 6.55E-03 | 5.59E-02 | 33 |
| hsa-miR-103-2* | 0.51 | 0.74 | 6.55E-03 | 5.59E-02 | 34 |
| hsa-miR-3937 | 2.04 | 1.09 | 6.99E-03 | 5.76E-02 | 35 |
| hsa-miR-548o | 0.45 | 0.68 | 7.14E-03 | 5.76E-02 | 36 |
| hsa-let-7i | 0.33 | 2.04 | 7.39E-03 | 5.79E-02 | 37 |
| hsa-miR-373* | 1.90 | 0.55 | 8.37E-03 | 5.87E-02 | 38 |
| hsa-miR-484 | 0.54 | 0.69 | 8.67E-03 | 5.87E-02 | 39 |
| hsa-miR-338-3p | | 0.71 | 8.73E-03 | 5.87E-02 | 40 |
| hsa-miR-1282 | 0.50 | 0.26 | 8.95E-03 | 5.87E-02 | 41 |
| hsa-miR-4327 | 1.95 | 1.09 | 9.05E-03 | 5.87E-02 | 42 |
| hsa-miR-550b | | 1.15 | 9.38E-03 | 5.87E-02 | 43 |
| hsa-miR-106b* | | 0.83 | 9.48E-03 | 5.87E-02 | 44 |
| hsa-miR-663 | 1.88 | 1.10 | 9.59E-03 | 5.87E-02 | 45 |
| hsa-miR-17* | 0.51 | 1.05 | 9.60E-03 | 5.87E-02 | 46 |
| hsa-miR-30c-1* | 2.31 | 0.34 | 9.86E-03 | 5.87E-02 | 47 |
| hsa-miR-665 | 1.87 | 0.86 | 1.00E-02 | 5.87E-02 | 48 |
| hsa-miR-363 | 0.44 | 1.56 | 1.04E-02 | 5.87E-02 | 49 |
| hsa-miR-144 | 0.46 | 1.19 | 1.06E-02 | 5.87E-02 | 50 |
| hsa-miR-514b-5p | 2.09 | 0.66 | 1.09E-02 | 5.87E-02 | 51 |
| hsa-miR-324-5p | | 0.71 | 1.09E-02 | 5.87E-02 | 52 |
| hsa-miR-92a | 0.55 | 1.11 | 1.09E-02 | 5.87E-02 | 53 |
| hsa-miR-183 | | 1.16 | 1.12E-02 | 5.87E-02 | 54 |
| hsa-miR-498 | 1.86 | 0.61 | 1.15E-02 | 5.87E-02 | 55 |
| hsa-miR-652 | 0.52 | 1.14 | 1.17E-02 | 5.87E-02 | 56 |
| hsa-miR-1914* | 1.89 | 0.62 | 1.18E-02 | 5.87E-02 | 57 |
| hsa-miR-451 | 0.49 | 0.44 | 1.18E-02 | 5.87E-02 | 58 |
| hsa-miR-25 | 0.54 | 1.57 | 1.20E-02 | 5.87E-02 | 59 |
| hsa-miR-4270 | 1.95 | 0.78 | 1.22E-02 | 5.87E-02 | 60 |
| hsa-miR-1202 | 2.03 | 0.58 | 1.23E-02 | 5.87E-02 | 61 |
| hsa-miR-1908 | 1.84 | 0.86 | 1.27E-02 | 5.87E-02 | 62 |
| hsa-miR-1268 | 1.90 | 0.79 | 1.28E-02 | 5.87E-02 | 63 |

TABLE 2-continued

| | | | | | |
|---|---|---|---|---|---|
| hsa-miR-532-5p | 0.53 | 1.17 | 1.30E-02 | 5.90E-02 | 64 |
| hsa-miR-28-5p | | 0.93 | 1.35E-02 | 5.91E-02 | 65 |
| hsa-miR-29b | 0.53 | 1.17 | 1.35E-02 | 5.91E-02 | 66 |
| hsa-let-7c | 0.41 | 2.31 | 1.36E-02 | 5.91E-02 | 67 |
| hsa-miR-20a | 0.41 | 2.35 | 1.45E-02 | 6.08E-02 | 68 |
| hsa-miR-122 | 2.33 | 1.12 | 1.47E-02 | 6.08E-02 | 69 |
| hsa-miR-548k | 0.53 | 0.53 | 1.52E-02 | 6.08E-02 | 70 |
| hsa-miR-149* | 1.88 | 1.04 | 1.53E-02 | 6.08E-02 | 71 |
| hsa-miR-4289 | 0.55 | 0.72 | 1.53E-02 | 6.08E-02 | 72 |
| hsa-miR-150* | 1.84 | 0.70 | 1.53E-02 | 6.08E-02 | 73 |
| hsa-miR-223* | | 0.96 | 1.59E-02 | 6.11E-02 | 74 |
| hsa-miR-18a* | 0.56 | 0.65 | 1.60E-02 | 6.11E-02 | 75 |
| hsa-miR-550a* | | 0.93 | 1.60E-02 | 6.11E-02 | 76 |
| hsa-miR-454* | 0.52 | 0.13 | 1.62E-02 | 6.11E-02 | 77 |
| hsa-miR-133b | 0.54 | 0.48 | 1.73E-02 | 6.31E-02 | 78 |
| hsa-miR-1469 | 1.76 | 1.11 | 1.74E-02 | 6.31E-02 | 79 |
| hsa-miR-939 | 2.02 | 1.36 | 1.74E-02 | 6.31E-02 | 80 |
| hsa-miR-186 | 0.57 | 0.71 | 1.78E-02 | 6.35E-02 | 81 |
| hsa-miR-3162 | 2.18 | 0.90 | 1.80E-02 | 6.35E-02 | 82 |
| hsa-miR-26a | 0.48 | 1.83 | 1.82E-02 | 6.35E-02 | 83 |
| hsa-let-7e | 0.52 | 0.92 | 1.85E-02 | 6.37E-02 | 84 |
| hsa-miR-3621 | 1.79 | 0.88 | 1.88E-02 | 6.37E-02 | 85 |
| hsa-miR-92b | 0.56 | 1.22 | 1.90E-02 | 6.37E-02 | 86 |
| hsa-miR-15b | 0.51 | 1.51 | 1.93E-02 | 6.37E-02 | 87 |
| hsa-miR-3202 | 2.13 | 0.60 | 1.93E-02 | 6.37E-02 | 88 |
| hsa-miR-146b-5p | 0.55 | 1.36 | 2.03E-02 | 6.61E-02 | 89 |
| hsa-miR-4306 | 0.58 | 1.37 | 2.11E-02 | 6.80E-02 | 90 |
| hsa-miR-590-5p | 0.57 | 1.26 | 2.28E-02 | 7.25E-02 | 91 |
| hsa-miR-339-3p | | 0.83 | 2.44E-02 | 7.66E-02 | 92 |
| hsa-miR-15a | 0.44 | 1.41 | 2.46E-02 | 7.66E-02 | 93 |
| hsa-let-7b | 0.47 | 2.34 | 2.53E-02 | 7.81E-02 | 94 |
| hsa-miR-551a | 0.54 | 0.34 | 2.88E-02 | 8.53E-02 | 95 |
| hsa-miR-342-3p | 0.59 | 1.45 | 2.88E-02 | 8.53E-02 | 96 |
| hsa-miR-362-5p | | 0.79 | 2.91E-02 | 8.53E-02 | 97 |
| hsa-miR-199a-5p | 0.56 | 1.08 | 2.91E-02 | 8.53E-02 | 98 |
| hsa-miR-1293 | 0.56 | 0.49 | 2.93E-02 | 8.53E-02 | 99 |

TABLE 2-continued

| | | | | | |
|---|---|---|---|---|---|
| hsa-miR-96 | | 0.73 | 2.94E-02 | 8.53E-02 | 100 |
| hsa-miR-3911 | 1.76 | 0.80 | 3.00E-02 | 8.61E-02 | 101 |
| hsa-miR-122* | 1.83 | | 3.08E-02 | 8.63E-02 | 102 |
| hsa-miR-185 | 0.60 | 1.50 | 3.09E-02 | 8.63E-02 | 103 |
| hsa-miR-195 | 0.48 | 1.42 | 3.09E-02 | 8.63E-02 | 104 |
| hsa-miR-29c* | | 0.76 | 3.14E-02 | 8.63E-02 | 105 |
| hsa-miR-140-3p | 0.57 | 1.63 | 3.15E-02 | 8.63E-02 | 106 |
| hsa-miR-1290 | 1.71 | 0.67 | 3.23E-02 | 8.76E-02 | 107 |
| hsa-miR-182 | 0.58 | 1.57 | 3.29E-02 | 8.82E-02 | 108 |
| hsa-miR-205 | 0.56 | 0.71 | 3.43E-02 | 9.01E-02 | 109 |
| hsa-miR-638 | 1.71 | 1.05 | 3.44E-02 | 9.01E-02 | 110 |
| hsa-miR-1182 | 1.73 | 0.60 | 3.45E-02 | 9.01E-02 | 111 |
| hsa-miR-103 | 0.49 | 1.81 | 3.54E-02 | 9.17E-02 | 112 |
| hsa-miR-223 | 0.50 | 1.21 | 3.66E-02 | 9.39E-02 | 113 |
| hsa-miR-423-3p | 0.61 | 1.08 | 3.77E-02 | 9.58E-02 | 114 |
| hsa-miR-128 | 0.62 | 1.20 | 3.87E-02 | 9.77E-02 | 115 |
| hsa-miR-199a-3p;hsa-miR-199b-3p | 0.50 | 1.50 | 3.92E-02 | 9.80E-02 | 116 |

EXAMPLE 2

The above-described microarray data is qualitative in nature. It is important to submit the findings to a quantitative interrogation such as RTqPCR. Thus, in this example, assays were carried out for confirming the above-mentioned 12 microRNAs through an independent method so as to achieve the goal of identifying signature microRNAs as a blood based microRNA biomarker.

To that end, the TaqMan™ MicroRNA Assays (Applied Biosystems, Foster City, Calif.) were used to verify the microRNAs in expanded sample pool. Expanding the study sample as outlined below allowed for greater validation and new cohorts for data analysis. More specifically, analysis of blood from an additional 65 subjects, including 30 stage 2A/2B pancreatic cancer, 10 high risk subjects, 10 unrelated malignant tumors, 5 benign cystic neoplasm of the pancreas, 5 chronic pancreatitis, and 5 healthy volunteers.

Of particular interest, inclusion of the high risk cohort has significant utility to gain critical insight into early detection. Since approximately 10% of pancreatic cancers are hereditary in origin (Klein et al. Cancer J 2001; 7:266-73; Bartsch et al. Int J Cancer 2004; 110:902-6; and Hemminki et al. Int J Cancer 2003; 103:525-30) and in some individuals the lifetime risk of pancreatic cancer approaches 50% (Rulyak et al. Pancreatology 2001; 1(5):477-85), a microRNA signature for screening and surveillance would be significant.

Briefly, whole blood was obtained from each patient and plasma extracted using a standard method (Ho et al., Transl Oncol. 2010; 3:109-113). Then, real-time quantitative polymerase chain reaction (real-time qPCR) for miRNA expression analysis was carried out. The levels of the above-mentioned miRs were determined by stem loop real-time qPCR using gene-specific TaqMan™ minor groove binding (MGB) primers according to the TaqMan MicroRNA Assay protocol (Applied Biosystems, Foster City, Calif.).

Each miRNA was amplified individually and in triplicate. Default threshold settings were used to determine threshold cycle (CT). Comparative CT method ($2^{-\Delta CT}$) was used for relative quantification of miRNA expression. MiR-3196 was used as normalizer because this miRNA showed minimal variation. The relative expression levels of each miRNA in comparison to the normalizer were then calculated using the formula $2^{-\Delta CT}$ where $\Delta CT$ represents the difference between each target gene and the normalizer (average CT for the target minus average CT for miR-3196). Shown below is a data processing procedure:

1. Raw CT values from 384 wells and 96 wells of the RT-PCR plates were exported from RQ Manager 1.2.1 to obtain 'Raw' values, they were presented in 'qPCR_miR*' tabs.
2. Excel formulas were used to pull CT values from the 'Raw' data to obtain the 'Raw_CTs' values.
3. The undetermined wells were replaced with 'ND' to obtain the 'Adjusted-CTs' values and correlation between 384 well and 96 well data was computed.
4. For each sample, the sample mean was calculated by averaging the triplicate data points and 'ND' were substituted with the least detected CT value (CT-->40) to obtain the 'MeanCTs' values.
5. miR-3196 which had low stdevs across the samples was chosen as the Normalization Control miRNA.
6. For each miRNA, the miRNA mean across the sample was calculated including the normalization control.

7. For each sample, the mean CT of the normalization control (miR-3196) was subtracted from the sample CT value to obtain the 'ΔCT' values.
8. The grand mean of the normalization control was subtracted from each miRNA mean to obtain the 'ΔCT' value of the miRNA mean.
9. For each sample, the 'ΔCT' value of the miRNA mean was subtracted from sample 'ΔCT' value to obtain the 'ΔΔCT' values.
10. Relative Quantities (RQ) were calculated using the formula RQ=2^−(ΔΔCT), using the 'ΔΔCT' values, and presented in the 'RQ' tab.
11. The ANOVA test results (see Statistical Analysis box below) were also presented in the 'RQ' tab.

For statistical analysis, the Anova analysis was used based on a one-way anova package from R. For each miRNA, the anova was tested across three different groups (Cancer, Healthy Control and High-risk). Normalized data sets from both RTQ-PCR and Microarray were used for 'RTQPCR-Microarray-Comparison.' 'ΔCT' values were used as the normalized dataset for RQPCR. The results are shown in Table 3 below. As shown in the table, miR-18a, miR-22, miR-486, miR-642b, miR-7, and miR-885-5p exhibited higher expression levels in cancer patients than in health control.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

TABLE 3

| | RTQ-PCR | | | | | | Microarray | | | | | |
| --- | --- | --- | --- | --- | --- | --- | --- | --- | --- | --- | --- | --- |
| | Fold Changes | | | Mean | | | Fold Changes | | | Mean | | |
| miRNA Name | Cancer vs. Control | High Risk vs. Control | Cancer vs. High Risk | Cancer | Healthy Control | High Risk | Cancer vs. Control | High Risk vs. Control | Cancer vs. High Risk | Cancer | Healthy Control | High Risk |
| miR-18a | 3.99 | 0.89 | 4.50 | 0.076 | 2.074 | 2.247 | 0.41 | 1.60 | 0.26 | 8.320 | 9.615 | 10.289 |
| miR-22 | 10.50 | 0.34 | 30.57 | −2.782 | 0.610 | 2.152 | 1.21 | 1.28 | 0.94 | 14.148 | 13.871 | 14.232 |
| miR-3196 | 1.00 | 1.00 | 1.00 | 0.000 | 0.000 | 0.000 | 1.45 | 1.34 | 1.08 | 13.260 | 12.720 | 13.143 |
| miR-3648 | 0.76 | 0.38 | 2.00 | 4.653 | 4.261 | 5.656 | 1.41 | 0.98 | 1.43 | 14.850 | 14.359 | 14.330 |
| miR-4253 | 0.60 | 0.69 | 0.87 | 5.037 | 4.295 | 4.837 | 2.58 | 0.97 | 2.65 | 12.481 | 11.115 | 11.074 |
| miR-486 | 2.90 | 1.74 | 1.67 | −6.528 | −4.989 | −5.786 | 0.37 | 1.06 | 0.35 | 13.199 | 14.628 | 14.706 |
| miR-642b | 1.37 | 0.18 | 7.46 | 2.769 | 3.227 | 5.668 | 2.90 | 0.89 | 3.25 | 10.792 | 9.255 | 9.093 |
| miR-7 | 11.44 | 1.04 | 11.05 | 0.934 | 4.450 | 4.400 | 0.42 | 0.78 | 0.54 | 5.847 | 7.105 | 6.745 |
| miR-885-5p | 11.42 | 0.87 | 13.17 | −0.136 | 3.377 | 3.583 | 2.52 | 0.62 | 4.05 | 9.183 | 7.851 | 7.166 |

Note:
Mean value for RTQ-PCR was calculated from the 'ΔCT' value. For correlation purpose, two samples c011-b and HR011-b (011-HR) that were not present in the microarray study were dropped Note:
Mean Value for Microarray was calculated from the final Log2-transformed, averaged and normalized probe intensities.

What is claimed is:

1. An array comprising
a support having a plurality of unique locations,
a first nucleic acid having a first sequence complementary to a first microRNA selected from the group consisting of miR-18a, miR-22, miR-486, miR-7, and miR-885-5p and
a second nucleic acid having a second sequence that is complementary to the sequence of miR-642b and hybridizes to the sequence of miR-642b under a stringent condition,
wherein each nucleic acid is immobilized to a unique location of the support,
wherein the first sequence and the second sequence are 15-200 bases in length.

2. The array of claim 1, wherein said first microRNA is miR-885-5p.

3. The array of claim 1, wherein the array comprises nucleic acids having sequences that are complementary to miR-18a, miR-22, miR-486, miR-642b, miR-7, and miR-885-5p, respectively.

4. The array of claim 1, wherein each nucleic acid is complementary to a sequence selected from the group consisting of SEQ ID NOs: 1-6.

5. A kit comprising
a first labeled probe having a first nucleic acid sequence complementary to a first microRNA selected from the group consisting of miR-18a, miR-22, miR-486, miR-7, and miR-885-5p, and
a second labeled probe having a second nucleic acid sequence that is complementary to the sequence of miR-642b and hybridizes to the sequence of miR-642b under a stringent condition,
wherein each probe is linked with a detection label selected from the group consisting of a fluorophore, a dye, a radiolabel, an enzyme, and a biotin,
wherein the first nucleic acid sequence and the second nucleic acid sequence are 15-200 bases in length.

6. The kit of claim 5, wherein said first microRNA is miR-885-5p.

7. The kit of claim 5, wherein the kit comprises labeled probes having sequences that are complementary to miR-18a, miR-22, miR-486, miR-642b, miR-7, and miR-885-5p, respectively.

8. The kit of claim 5, further comprising reagents for performing hybridization or an array.

9. The kit of claim 5, further comprising reagents for performing PCR.

10. The kit of claim 5, wherein the probe is complementary to a sequence selected from the group consisting of SEQ ID NOs: 1-6.

* * * * *